(12) United States Patent
Okamoto et al.

(10) Patent No.: US 10,400,649 B2
(45) Date of Patent: Sep. 3, 2019

(54) AMMONIA SENSOR CALIBRATION METHOD

(71) Applicant: NGK INSULATORS, LTD., Nagoya-shi, Aichi (JP)

(72) Inventors: Taku Okamoto, Nagoya (JP); Kosuke Monna, Frankfurt am Main (DE); Nobuhiko Mori, Nagoya (JP)

(73) Assignee: NGK Insulators, Ltd., Nagoya (JP)

( * ) Notice: Subject to any disclaimer, the term of this patent is extended or adjusted under 35 U.S.C. 154(b) by 0 days.

(21) Appl. No.: 15/862,667

(22) Filed: Jan. 5, 2018

(65) Prior Publication Data

US 2018/0195426 A1 Jul. 12, 2018

(30) Foreign Application Priority Data

Jan. 10, 2017 (JP) .................. 2017-002074

(51) Int. Cl.
*F01N 3/20* (2006.01)
*C01B 21/04* (2006.01)
*C01C 1/02* (2006.01)
*G01N 33/00* (2006.01)
(Continued)

(52) U.S. Cl.
CPC .......... *F01N 3/208* (2013.01); *C01B 21/0422* (2013.01); *C01C 1/026* (2013.01); *C01C 1/086* (2013.01); *F01N 11/00* (2013.01); *G01N 33/0006* (2013.01); *F01N 2560/026* (2013.01); *Y02T 10/24* (2013.01); *Y02T 10/47* (2013.01)

(58) Field of Classification Search
CPC ..... C01B 21/0422; C01C 1/026; C01C 1/086; F01N 11/00; F01N 3/208; F01N 2560/026; G01N 33/0006; Y02T 10/24; Y02T 10/47
USPC .......................... 60/274, 277, 295, 299, 301
See application file for complete search history.

(56) References Cited

U.S. PATENT DOCUMENTS

| 2013/0104638 A1* | 5/2013 | Takahashi | ............... F01N 3/208 73/114.71 |
|---|---|---|---|
| 2014/0373511 A1* | 12/2014 | Osburn | .............. B01D 53/9431 60/274 |
| 2015/0128565 A1* | 5/2015 | Upadhyay | ................. F01N 3/18 60/274 |

FOREIGN PATENT DOCUMENTS

JP 2014-224504 A 12/2014

* cited by examiner

*Primary Examiner* — Patrick D Maines
*Assistant Examiner* — Dapinder Singh
(74) *Attorney, Agent, or Firm* — Mattingly & Malur, PC

(57) ABSTRACT

A slope $\Delta^{t1}{}_{HC}$ in a linear area of sensor output characteristics for a mixed atmosphere of CO and THC and a slope $\Delta^{t1}{}_{NH}$ in the linear area of the sensor output characteristics for $NH_3$ are specified in advance at a time when a time t1 has elapsed since a start of use of an engine. In performing calibration of an $NH_3$ sensor when a time t2 (greater than the time t1) has elapsed, a slope $\Delta^{t2}{}_{HC}$ in the linear area of the sensor output characteristics for the mixed atmosphere is specified, a value $\Delta^{t2}{}_{NH}$ is calculated from an equation $\Delta^{t2}{}_{NH} = \Delta^{t2}{}_{HC}/(\Delta^{t1}{}_{HC}/\Delta^{t1}{}_{NH})$, and the calculated value $\Delta^{t2}{}_{NH}$ is determined as a new slope in the linear area of the sensor output characteristics for an $NH_3$ gas.

18 Claims, 14 Drawing Sheets

(51) Int. Cl.
*F01N 11/00* (2006.01)
*C01C 1/08* (2006.01)

F I G. 1 3 A
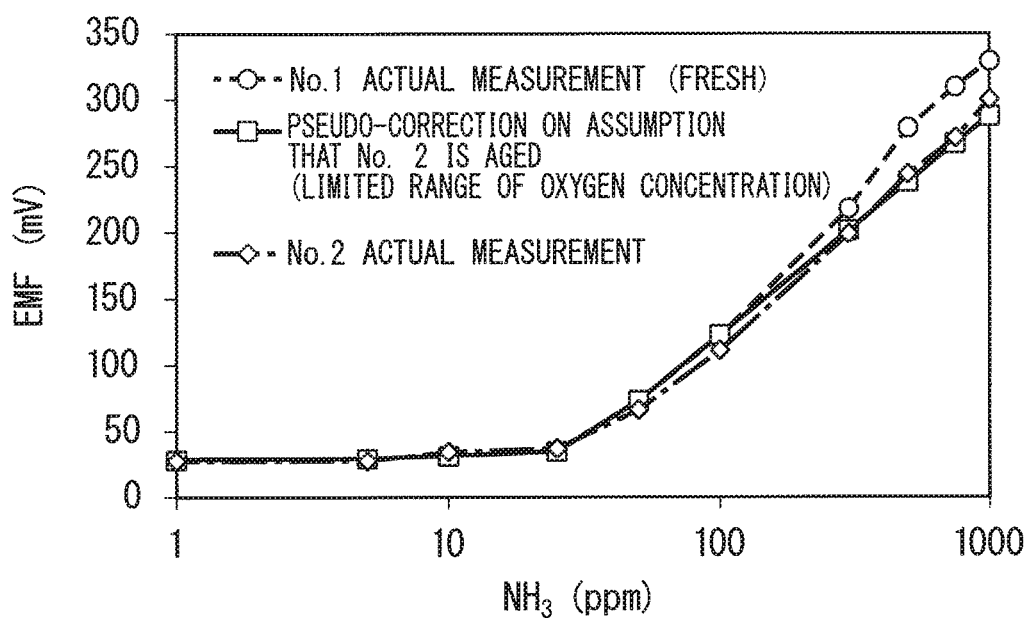
F I G. 1 3 B
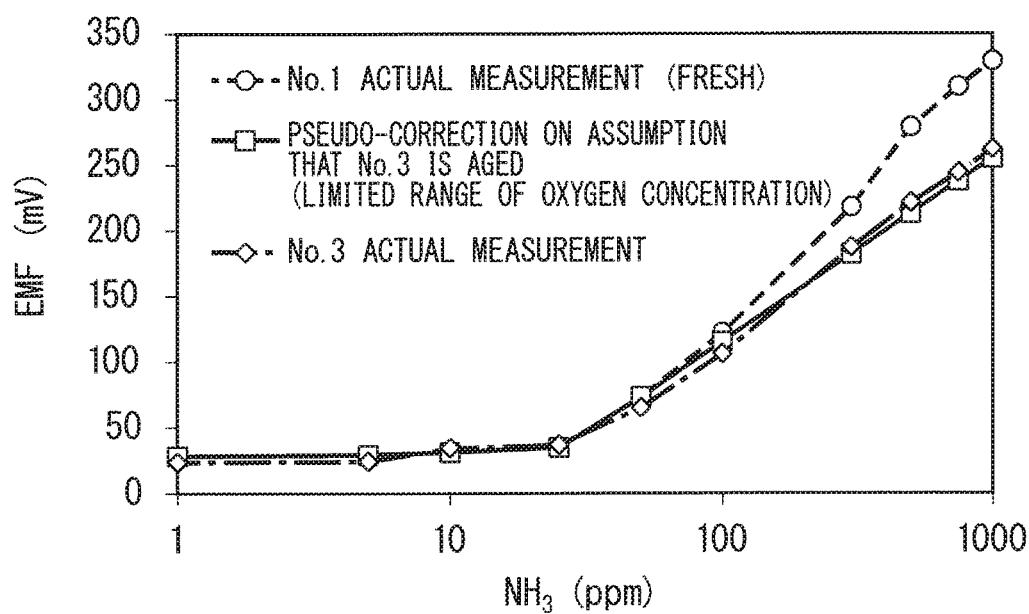

AMMONIA SENSOR CALIBRATION METHOD

BACKGROUND OF THE INVENTION

Field of the Invention

The present invention relates to calibration of an ammonia sensor and, in particular, to calibration of an ammonia sensor located downstream from an SCR on an exhaust path of a diesel engine.

Description of the Background Art

As an apparatus for purifying nitrogen oxides (NOx) included in an exhaust gas from a diesel engine, a selective catalytic reduction denitration apparatus (hereinafter, an SCR) that uses an aqueous urea solution or aqueous ammonia as a reductant is widely known (see, for example, Japanese Patent Application Laid-Open Publication No. 2014-224504). The SCR is usually located along an exhaust path of the diesel engine. A reduction catalyst included in the SCR facilitates a reduction reaction of the NOx included in the exhaust gas to ammonia generated through decomposition of the reductant, so that the NOx is purified by being decomposed into nitrogen, water, carbon dioxide, and the like.

When the SCR is used to purify the NOx in a manner as described above, ammonia may sometimes flow downstream from the SCR, depending on a supply of the reductant. To appropriately control the supply of the reductant, a sensor (an ammonia sensor) for obtaining an ammonia concentration is required to be located downstream from the SCR.

Japanese Patent Application Laid-Open Publication No. 2014-224504 discloses an ammonia sensor diagnostic apparatus that includes not only the ammonia sensor but also a NOx sensor for detecting NOx located downstream from the SCR, diagnoses the validity of a detection value from the ammonia sensor based on a detection value from the NOx sensor, and, if the detection value is not valid, corrects the detection value.

In some cases, however, depending on usage of the NOx sensor, an operating condition of an engine, and the like, the detection value from the NOx sensor itself is not valid. It is preferable to correct (calibrate) the ammonia sensor based on the detection value (an output value) from the ammonia sensor itself.

Japanese Patent Application Laid-Open Publication No. 2014-224504 discloses, as an example of the ammonia sensor to be used, an ammonia sensor including a solid electrolyte that conducts only one type of ions, but fails to disclose specific configuration and characteristics of the ammonia sensor.

SUMMARY

The present invention relates to calibration of an ammonia sensor and is directed, in particular, to calibration of an ammonia sensor located downstream from an SCR on an exhaust path of a diesel engine.

According to the present invention, an ammonia sensor calibration method is a method of calibrating output characteristics of an ammonia sensor for an ammonia gas. The ammonia sensor is located downstream from a selective catalytic reduction denitration apparatus on an exhaust path of a diesel engine. A relationship between a logarithmic value of a concentration of a predetermined gas component in an exhaust gas exhausted from the diesel engine and an output value from the ammonia sensor when the predetermined gas component is detected is defined as sensor output characteristics for the predetermined gas component. The ammonia sensor calibration method includes a) specifying in advance a slope $\Delta^{t1}_{HC}$ in a linear area of the sensor output characteristics for a mixed atmosphere of carbon monoxide and total hydrocarbons and a slope $\Delta^{t1}_{NH}$ in the linear area of the sensor output characteristics for an ammonia gas at a time when an arbitrary time t1 has elapsed since a start of use of the diesel engine; and b) performing calibration of the ammonia sensor when a time t2 has elapsed since the start of use of the diesel engine. The time t2 is greater than the time t1. The step b) includes: b-1) specifying a slope $\Delta^{t2}_{HC}$ in the linear area of the sensor output characteristics for the mixed atmosphere; b-2) calculating a value $\Delta^{t2}_{NH}$ from an equation $\Delta^{t2}_{NH} = \Delta^{t2}_{HC}/(\Delta^{t1}_{HC}/\Delta^{t1}_{NH})$; and b-3) determining the value $\Delta^{t2}_{NH}$ calculated in the step b-2) as a new slope in the linear area of the sensor output characteristics of the ammonia sensor for the ammonia gas.

According to the present invention, regarding to the ammonia sensor, which is located downstream from the SCR in an engine system, and has sensor output characteristics degraded with a continuous use of the engine system, the sensor output characteristics after degradation can suitably be specified based on the sensor output value obtained from the ammonia sensor itself. This means that calibration of the ammonia sensor can be performed with high accuracy based on the output value from the ammonia sensor itself.

An object of the present invention is to provide a technique of performing calibration of an ammonia sensor located downstream from an SCR on an exhaust path of a diesel engine with high accuracy.

These and other objects, features, aspects and advantages of the present invention will become more apparent from the following detailed description of the present invention when taken in conjunction with the accompanying drawings.

BRIEF DESCRIPTION OF THE DRAWINGS

FIG. 13A shows a result of calibration of the ammonia sensor No. 2, and FIG. 13B shows a result of calibration of the ammonia sensor No. 3.

DESCRIPTION OF THE PREFERRED EMBODIMENTS

<Overview of System>

Figure 1:
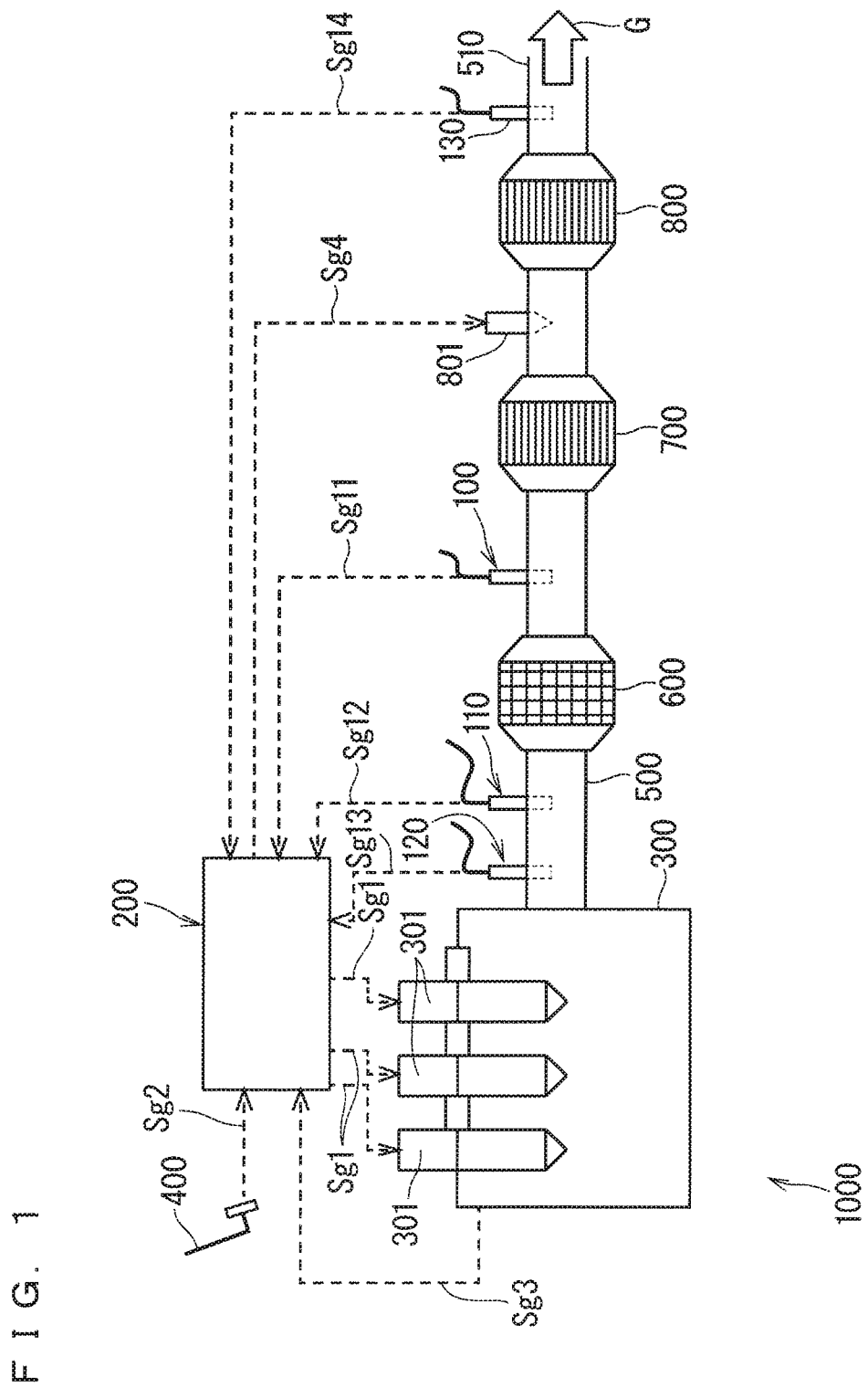
FIG. 1 shows schematic configuration of a diesel engine system 1000.

FIG. 1 shows schematic configuration of a diesel engine system (hereinafter, also simply referred to as an engine system) 1000 including an ammonia gas sensor (also referred to as an ammonia sensor and a $NH_3$ sensor) 130 as a target of calibration according to an embodiment of the present invention.

The diesel engine system 1000 mainly includes: a sensor group including the ammonia sensor 130, a hydrocarbon gas sensor (hereinafter, also referred to as an HC sensor) 100, a temperature sensor 110, and an oxygen sensor 120; an electronic controller 200 that is a controller for controlling an operation of the entire engine system 1000; an engine main body 300 that is a diesel engine of one type of an internal combustion engine; a plurality of fuel injection valves 301 that inject fuel into the engine main body 300; a fuel injection instruction part 400 for instructing the fuel injection valves 301 to inject the fuel; an exhaust pipe 500 forming an exhaust path that externally discharges an exhaust gas (engine exhaust) G generated in the engine main body 300; an oxidation catalyst (DOC) 600 located along the exhaust pipe 500; a diesel particle collection filter (DPF) 700; a selective catalytic reduction denitration apparatus (an SCR) 800; and a urea source 801 that supplies, as a reductant, urea to the SCR 800. In the present embodiment, in a relative meaning, the position closer to the engine main body 300 that is one side of the exhaust pipe 500 is referred to as an upstream side, and the position closer to an exhaust port 510 that is opposite the engine main body 300 is referred to as a downstream side. In addition to the above-mentioned components, the engine system 1000 includes an intake system (not illustrated) that supplies air to the engine main body 300.

The engine system 1000 is typically mounted in a vehicle, and in such a case, the fuel injection instruction part 400 is an accelerator pedal.

In the engine system 1000, the electronic controller 200 issues a fuel injection instruction signal sg1 to the fuel injection valves 301. The fuel injection instruction signal sg1 is usually issued in response to a fuel injection request signal sg2 for demanding an injection of a predetermined amount of fuel, which is provided from the fuel injection instruction part 400 to the electronic controller 200 during the operation (action) of the engine system 1000 (e.g., an accelerator pedal is depressed so that an optimum fuel injection reflecting a large number of parameters, such as the position of an accelerator, an amount of oxygen intake, an engine speed, and torque is demanded). In addition to this, the fuel injection instruction signal sg1 is issued for calibration of the ammonia sensor 130.

A monitor signal sg3 for monitoring various situations inside the engine main body 300 is provided from the engine main body 300 to the electronic controller 200.

In the engine system 1000, the exhaust gas G exhausted from the engine main body 300 that is a diesel engine is a gas in an excessive oxygen ($O_2$) atmosphere having an oxygen concentration of approximately 5% to 21%. The exhaust gas G contains, in addition to oxygen, an unburned hydrocarbon gas, a nitrogen oxide gas (hereinafter, simply referred to as NOx), and particulate matter (particles), such as soot (graphite). The unburned hydrocarbon gas is adsorbed or oxidized by the DOC 600, the particulate matter is collected by the DPF 700, and the NOx is decomposed by the SCR 800. The exhaust gas G purified by the action of the DOC 600, the DPF 700, and the SCR 800 is externally discharged from the exhaust port 510.

The unburned hydrocarbon gas to be processed by the DOC 600 contains not only typical hydrocarbon gases (classified as hydrocarbons by a chemical formula), such as $C_2H_4$, $C_3H_6$, and n-C8, but also carbon monoxide (CO). The HC sensor 100 can suitably detect a target gas, including CO. However, $CH_4$ is excluded.

The purification (decomposition) of the NOx in the SCR 800 is implemented in a manner that a reduction catalyst included in the SCR 800 facilitates a reduction reaction of the NOx to ammonia generated through decomposition of the urea supplied from the urea source 801 located upstream from the SCR 800 to decompose the NOx into nitrogen, water, carbon dioxide, and the like.

The HC sensor 100 is located downstream from the DOC 600 along the exhaust pipe 500, and detects the unburned hydrocarbon gas at the location. The temperature sensor 110 is located upstream from the DOC 600, and detects the temperature of the exhaust gas G (an exhaust temperature) at the location.

The oxygen sensor 120 detects $O_2$ (oxygen) included in the exhaust gas G. Although the oxygen sensor 120 is located upstream from the DOC 600 along the exhaust pipe 500 in FIG. 1, the oxygen sensor 120 may not necessarily be located upstream from the DOC 600, and may be disposed at an another location along the exhaust pipe 500.

Furthermore, the ammonia sensor 130 is located downstream from the SCR 800, and detects an ammonia gas concentration at the location.

One end portion of the HC sensor 100, one end portion of the temperature sensor 110, one end portion of the oxygen sensor 120, and one end portion of the ammonia sensor 130 have each been inserted in the exhaust pipe 500. An HC detection signal sg11, an exhaust temperature detection signal sg12, an oxygen detection signal sg13, and an ammonia detection signal sg14 issued from the respective sensors are each provided to the electronic controller 200.

The HC detection signal sg11 issued from the HC sensor 100 and the exhaust temperature detection signal sg12 issued from the temperature sensor 110 are used to monitor the catalytic ability of the DOC 600 and to diagnose whether the DOC 600 has been degraded, for example. The oxygen detection signal sg13 issued from the oxygen sensor 120 is used to control the supply of air in the intake system, but may also be used to diagnose degradation of the DOC 600.

Any known sensors, including a sensor used in a typical engine system to measure the exhaust temperature, may be used as the HC sensor 100, the temperature sensor 110, and the oxygen sensor 120.

On the other hand, the ammonia detection signal sg14 issued from the ammonia sensor 130 is used by the electronic controller 200 to control the supply of the urea from the urea source 801. An example of the configuration of the ammonia sensor 130 will be described in details below.

In addition to these sensors, the engine system 1000 may further include a NOx sensor for measuring a NOx concentration of the exhaust gas G located downstream from the SCR 800.

The electronic controller 200 includes a storage (not illustrated), such as memory and an HDD, and the storage stores a program for controlling the operation of the engine system 1000, various data used for calibration of the ammonia sensor 130, which will be described below, and the like.

<Example of Configuration of Ammonia Sensor>

Figure 2:
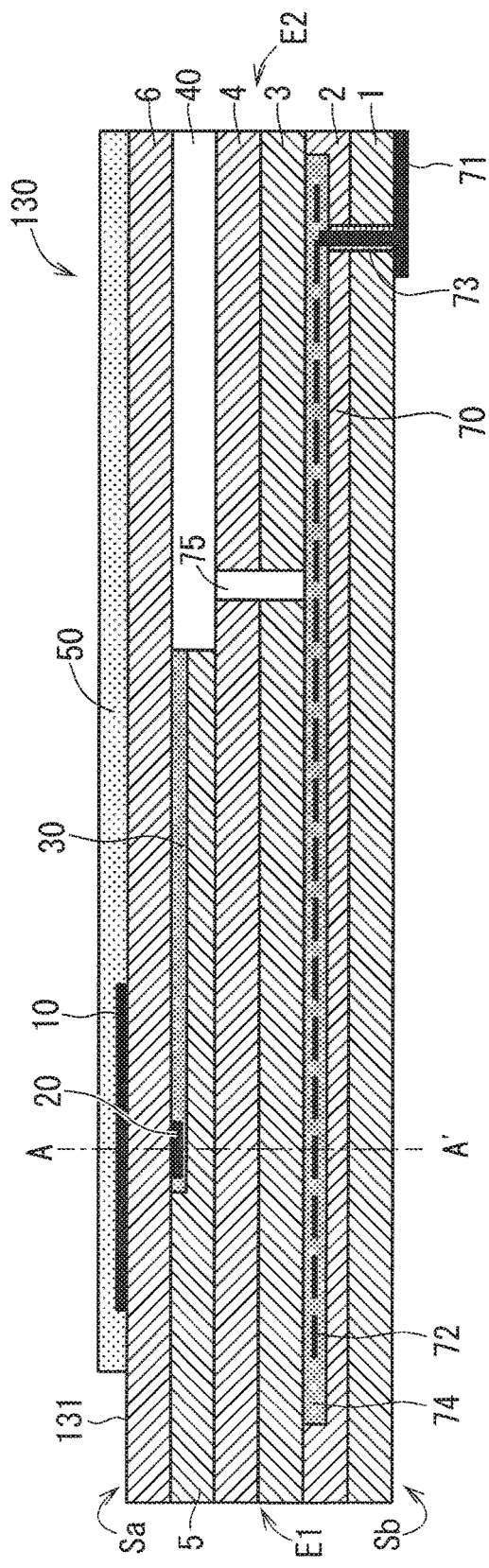
FIGS. 2A and 2B are schematic sectional views each schematically showing an example of the configuration of an ammonia sensor 130.

FIGS. 2A and 2B are schematic sectional views each schematically showing an example of the configuration of the ammonia sensor 130 used in the present embodiment. FIG. 2A is a vertical sectional view taken along the longitudinal direction of a sensor element 131, which is a main component of the ammonia sensor 130. FIG. 2B is a diagram including a cross section perpendicular to the longitudinal direction of the sensor element 131 taken along the line A-A' of FIG. 2A.

The ammonia sensor 130 used in the present embodiment is a so-called mixed potential gas sensor. Generally speaking, the ammonia sensor 130 uses a potential difference occurring between a detection electrode 10 located on the surface of the sensor element 131 mainly including a ceramic, which is an oxygen-ion conductive solid electrolyte, such as zirconia ($ZrO_2$), and a reference electrode 20 located inside the sensor element 131 due to the difference in concentration of a gas component to be measured around the detection electrode 10 and the reference electrode 20 based on the principle of mixed potential to obtain the concentration of the gas component of the measurement gas.

The sensor element 131 mainly includes, in addition to the detection electrode 10 and the reference electrode 20 described above, a reference gas introduction layer 30, a reference gas introduction space 40, and a surface protective layer 50.

In the present embodiment, the sensor element 131 has a structure in which six layers, namely, a first solid electrolyte layer 1, a second solid electrolyte layer 2, a third solid electrolyte layer 3, a fourth solid electrolyte layer 4, a fifth solid electrolyte layer 5, and a sixth solid electrolyte layer 6, each formed of an oxygen-ion conductive solid electrolyte, are laminated in the stated order from the bottom side of FIGS. 2A and 2B, and includes other components located mainly between these layers or on an outer peripheral surface of the element. Solid electrolytes forming these six layers are dense and airtight. The sensor element 131 is manufactured, for example, by performing predetermined machining and printing of circuit patterns with respect to ceramic green sheets corresponding to respective layers, then laminating these green sheets, and further firing the laminated green sheets for integration.

In the following description, an upper surface of the sixth solid electrolyte layer 6 is referred to as a front surface Sa of the sensor element 131, and a lower surface of the first solid electrolyte layer 1 is referred to as a rear surface Sb of the sensor element 131 in FIGS. 2A and 2B for convenience sake. When the ammonia gas concentration of the measurement gas is obtained using the ammonia sensor 130, the ammonia sensor 130 is located so that a predetermined range of the sensor element 131 at least including the detection electrode 10 from a distal end E1 as one end of the sensor element 131 is located in a measurement gas atmosphere, and the other portion of the sensor element 131 including a proximal end E2 as the other end of the sensor element 131 is not in contact with the measurement gas atmosphere.

The detection electrode 10 is an electrode for detecting the measurement gas. The detection electrode 10 is formed as a porous cermet electrode made of Pt containing a predetermined ratio of Au, namely, a Pt—Au alloy, and zirconia. The detection electrode 10 is located on a portion of the front surface Sa of the sensor element 131 closer to the distal end E1 as one end, in the longitudinal direction, of the sensor element 131 to be approximately rectangular in plan view. When the ammonia sensor 130 is used, the ammonia sensor 130 is located so that a portion of the sensor element 131 at least including the detection electrode 10 is exposed to the measurement gas.

The composition of the Pt—Au alloy of the detection electrode 10 is suitably set, so that the detection electrode 10 has catalytic activity inactivated for an ammonia gas in a predetermined concentration range. This means that a decomposition reaction of the ammonia gas in the detection electrode 10 is prevented or reduced. Thus, in the ammonia sensor 130, the potential of the detection electrode 10 selectively varies for (has correlation with) the ammonia gas in the predetermined concentration range in accordance with the concentration thereof. In other words, the detection electrode 10 is provided to have high concentration dependence of the potential for the ammonia gas in the predetermined concentration range while having low concentration dependence of the potential for other components of the measurement gas.

More specifically, in the sensor element 131 of the ammonia sensor 130, with an Au abundance ratio on the surfaces of Pt—Au alloy particles included in the detection electrode 10 being set to 0.3 or more, the detection electrode 10 is provided to have noticeable dependence of the potential on the ammonia gas concentration at least in a concentration range of 0 ppm to 1000 ppm. This means that the detection electrode 10 is provided to be capable of suitably detecting the ammonia gas in the concentration range of 0 ppm to 1000 ppm.

In this specification, the Au abundance ratio means an area ratio of a portion covered with Au to a portion at which Pt is exposed in the surface of noble metal particles included in the detection electrode 10. In this specification, the Au abundance ratio is calculated from an expression shown below using Au and Pt detection values in an Auger spectrum obtained by performing Auger electron spectroscopy (AES) analysis on the surface of the noble metal particles.

Au abundance ratio=Au detection value/Pt detection value         (1)

The Au abundance ratio is one when the area of the portion at which Pt is exposed and the area of the portion covered with Au are equal to each other.

The Au abundance ratio can also be calculated using a relative sensitivity coefficient method from a peak intensity of a peak detected for Au and Pt obtained by subjecting the surface of the noble metal particles to X-ray photoelectron spectroscopy (XPS) analysis. The value of the Au abundance ratio obtained by this method can be considered to be substantially the same as the value of the Au abundance ratio calculated based on the result of AES analysis.

The volume ratio of noble metal components to zirconia in the detection electrode 10 is approximately 5:5 to 8:2.

The detection electrode 10 preferably has a porosity of 10% or more and 30% or less and a thickness of 5 μm or more to cause the ammonia sensor 130 to suitably express its function.

Although a planar size of the detection electrode 10 may be set appropriately, the size in the longitudinal direction of the sensor element is approximately 0.2 mm to 10 mm, and a size in a direction perpendicular to the longitudinal direction of the sensor element is approximately 1 mm to 5 mm, for example.

The reference electrode 20 is an electrode that is located inside the sensor element 131, is used as a reference when the concentration of the measurement gas is obtained, and is approximately rectangular in plan view. The reference electrode 20 is formed as a porous cermet electrode made of Pt and zirconia.

The reference electrode 20 is formed to have a porosity of 10% or more and 30% or less, and a thickness of 5 μm or more and 15 μm or less. A planar size of the reference electrode 20 may be smaller than that of the detection electrode 10 as illustrated in FIGS. 2A and 2B, or may be similar to that of the detection electrode 10.

The reference gas introduction layer 30 is a layer formed of porous alumina located inside the sensor element 131 to cover the reference electrode 20, and the reference gas introduction space 40 is an internal space located closer to the proximal end E2 of the sensor element 131. Atmospheric air (oxygen) as a reference gas when the ammonia gas concentration is obtained is externally introduced into the reference gas introduction space 40.

The reference gas introduction space 40 and the reference gas introduction layer 30 communicate with each other, so that the surroundings of the reference electrode 20 are always filled with the atmospheric air (oxygen) through the reference gas introduction space 40 and the reference gas introduction layer 30 when the ammonia sensor 130 is used. The reference electrode 20 thus always has a constant potential when the ammonia sensor 130 is used.

The reference gas introduction space 40 and the reference gas introduction layer 30 are prevented from being in contact with the measurement gas by the surrounding solid electrolytes, so that the reference electrode 20 is not in contact with the measurement gas even when the detection electrode 10 is exposed to the measurement gas.

In a case illustrated in FIG. 2A, the reference gas introduction space 40 is provided so that a part of the fifth solid electrolyte layer 5 is caused to be a space communicating with the outside at the location closer to the proximal end E2 of the sensor element 131. The reference gas introduction layer 30 is provided between the fifth solid electrolyte layer 5 and the sixth solid electrolyte layer 6 to extend in the longitudinal direction of the sensor element 131. The reference electrode 20 is located below the center of gravity of the detection electrode 10 in FIG. 2A.

The surface protective layer 50 is a porous layer formed of alumina located on the front surface Sa of the sensor element 131 to at least cover the detection electrode 10. The surface protective layer 50 is provided as an electrode protective layer for preventing or reducing degradation of the detection electrode 10 caused by continuous exposure to the measurement gas when the ammonia sensor 130 is used. In a case illustrated in FIGS. 2A and 2B, the surface protective layer 50 is provided to cover not only the detection electrode 10 but also the almost entire front surface Sa of the sensor element 131 except for a predetermined range from the distal end E1 of the sensor element 131.

The surface protective layer 50 has a thickness of 10 μm to 50 μm and a pore diameter of 1 μm or less, and preferably has a porosity of 5% or more and 40% or less. A porosity less than 5% is not preferable as the measurement gas does not suitably reach the detection electrode 10, leading to poor responsiveness of the ammonia sensor 130. A porosity more than 40% is not preferable as adhesion of a poisoning substance to the detection electrode 10 and the like are likely to occur, and a function of protecting the detection electrode 10 cannot sufficiently be performed.

In the present embodiment, the porosity is evaluated through image analysis of an enlarged cross-sectional SEM image (an enlarged secondary electron image) (Description of "Ceramic Processing", Nobuyasu Mizutani et al., Gihodo Shuppan Co., Ltd., is referred to).

As illustrated in FIG. 2B, the ammonia sensor 130 includes a potentiometer 60 that can measure a potential difference between the detection electrode 10 and the reference electrode 20. Although wiring between the detection electrode 10 and the potentiometer 60 and between the reference electrode 20 and the potentiometer 60 is simplified in FIG. 2B, in the actual sensor element 131, connection terminals (not illustrated) are located on a portion of the front surface Sa or the rear surface Sb closer to the proximal end E2 to correspond to the respective electrodes, and wiring patterns (not illustrated) connecting the electrodes to the corresponding connection terminals are formed on the front surface Sa and inside the element. The detection electrode 10 and the reference electrode 20 are each electrically connected to the potentiometer 60 through the wiring patterns and the connection terminals. In the present embodiment, the potential difference between the detection electrode 10 and the reference electrode 20 measured by the potentiometer 60 is the ammonia detection signal sg14. The potential difference is also referred to as a sensor output.

The sensor element 131 further includes a heater part 70 playing a role in temperature adjustment of heating the sensor element 131 and keeping it warm to enhance the oxygen ion conductivity of the solid electrolytes. The heater part 70 includes a heater electrode 71, heaters 72, a through hole 73, a heater insulating layer 74, and a pressure diffusion hole 75.

The heater electrode 71 is an electrode formed to be in contact with the rear surface Sb of the sensor element 131 (the lower surface of the first solid electrolyte layer 1 in FIGS. 2A and 2B). The heater electrode 71 is to be connected to an external power supply (not illustrated) to enable the heater part 70 to be externally powered.

The heaters 72 are electric resistors located inside the sensor element 131. The heaters 72 are connected to the heater electrode 71 via the through hole 73, and generate heat by being externally powered through the heater electrode 71 to heat the solid electrolytes forming the sensor element 131 and keep them warm.

In the case illustrated in FIGS. 2A and 2B, the heaters 72 are buried across a region extending from the proximal end E2 to the location below the detection electrode 10 close to the distal end E1 to be vertically sandwiched between the second solid electrolyte layer 2 and the third solid electrolyte layer 3. The heaters 72 can thus adjust the sensor element 131 as a whole to a temperature at which the solid electrolytes are activated.

The heater insulating layer 74 is an insulating layer formed of an insulator, such as alumina, on upper and lower surfaces of the heaters 72. The heater insulating layer 74 is formed for electrical insulation between the second solid electrolyte layer 2 and the heaters 72 and for electrical insulation between the third solid electrolyte layer 3 and the heaters 72.

The pressure diffusion hole 75 is a part provided to penetrate the third solid electrolyte layer 3 and the fourth solid electrolyte layer 4 to communicate with the reference gas introduction space 40, and is formed to mitigate an internal pressure rise associated with a temperature rise in the heater insulating layer 74.

When the ammonia gas concentration of the exhaust gas G existing downstream from the SCR 800 as the measurement gas is obtained using the ammonia sensor 130 having configuration as described above, the ammonia sensor 130 is located so that only the predetermined range of the sensor element 131 at least including the detection electrode 10 from the distal end E1 is inserted in the exhaust pipe 500 of the engine system 1000, while the portion of the sensor element 131 closer to the proximal end E2 is isolated from the space as described above, and the atmospheric air (oxygen) is supplied to the reference gas introduction space 40. The heaters 72 heat the sensor element 131 to an appropriate temperature of 300° C. to 800° C., preferably to 400° C. to 700° C., and more preferably to 400° C. to 600° C.

In this state, a potential difference occurs between the detection electrode 10, which is exposed to the measurement gas (exhaust gas G), and the reference electrode 20, which is located in the atmospheric air. As described above, however, the potential of the detection electrode 10 selectively has concentration dependence for the ammonia gas of the measurement gas (exhaust gas G) while the potential of the reference electrode 20 located under the atmosphere of the atmospheric air (having a constant oxygen concentration) is maintained constant, and thus the potential difference (sensor output) has a value substantially corresponding to the concentration of the measurement gas around the detection electrode 10. The ammonia gas concentration and the sensor output thus have a constant functional relationship (referred to as sensor output characteristics or sensitivity characteristics). The ammonia gas concentration of the measurement gas can be obtained using the sensor output characteristics.

That is to say, prior to installation of the ammonia sensor 130 in the exhaust pipe 500, the sensor output characteristics are experimentally specified by measuring the sensor output in advance using, as the measurement gas, a plurality of different mixed gases having known ammonia gas concentrations, and the sensor output characteristics are stored in the electronic controller 200. In the engine system 1000 in which the ammonia sensor 130 is installed, the electronic controller 200 converts the sensor output varying moment by moment depending on the ammonia gas concentration of the measurement gas into the ammonia gas concentration based on the sensor output characteristics to obtain the ammonia gas concentration at the location downstream from the SCR 800 approximately in real time.

<Degradation of Ammonia Sensor and Calibration>

When the engine system 1000 is used continuously in the above-mentioned manner, the output value from the ammonia sensor 130 corresponding to a certain ammonia gas concentration has originally to be constant regardless of a time of measurement, but, in actuality, it is empirically known that the sensor output value decreases with a continuous use of the ammonia sensor 130. This is presumably because the detection electrode 10 is oxidized in the ammonia sensor 130 exposed to the exhaust gas G having a high temperature.

Figure 3:
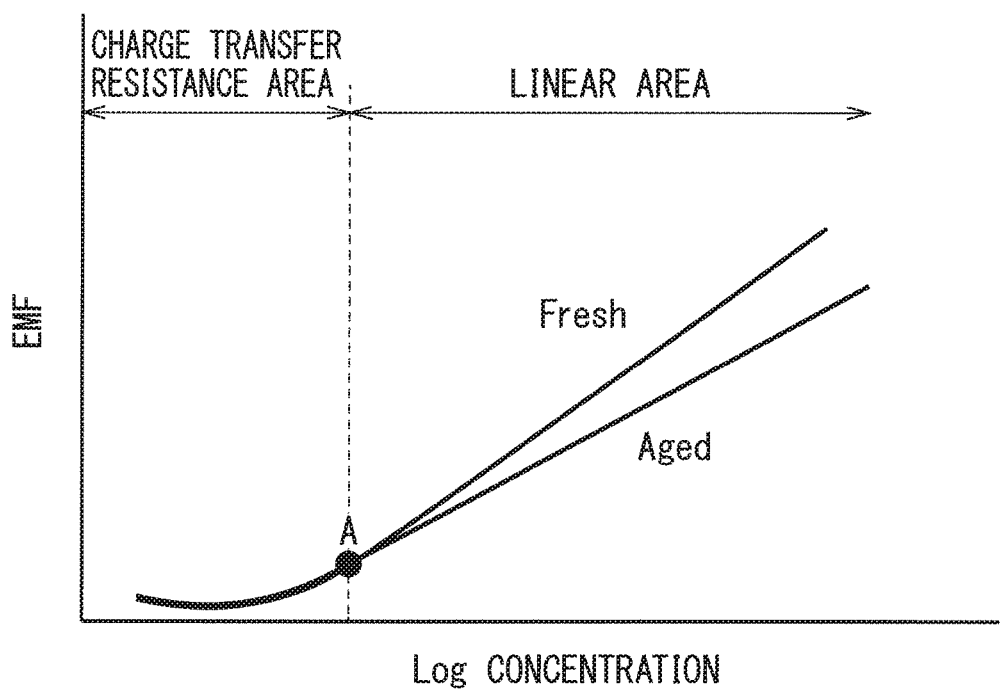
FIG. 3 schematically shows sensor output characteristics of the ammonia sensor 130.

FIG. 3 schematically shows the sensor output characteristics of the ammonia sensor 130. In FIG. 3, "Log CONCENTRATION" in the horizontal axis indicates a logarithmic value of the ammonia gas concentration, and EMF in the vertical axis means the "sensor output". In description of FIG. 3 and the subsequent description, the ammonia sensor before being used (being unused after the manufacture) is referred to as a "Fresh", a "Fresh one", and the like, and the ammonia sensor 130 having been used is referred to as an "Aged", an "Aged one", and the like. In FIG. 3, both the sensor output characteristics of the Fresh one and the sensor output characteristics of the Aged one are shown. In the subsequent description, the "sensor output characteristics" indicate a sensor output-concentration logarithmic value graph represented by a semilogarithmic plot as illustrated in FIG. 3, and a slope in a linear area of the sensor output characteristics is simply referred to as a "slope" of the sensor output characteristics unless otherwise noted.

As can be seen from FIG. 3, in an area in which the ammonia gas concentration is higher than that at a certain point A, the sensor output (EMF) varies linearly with the logarithmic value of the ammonia gas concentration. In the subsequent description, the area is referred to as a linear area. The variation in the linear area is in line with a mixed potential theory. On the other hand, the linear variation is not shown in an area in which the ammonia gas concentration is lower than that at the point A. This is because the sensor output does not follow the mixed potential due to a large contribution of charge transfer resistance in the area. In the subsequent description, the area is referred to as a charge transfer resistance area. The point A is also referred to as a starting point of the charge transfer resistance area.

In the charge transfer resistance area, the sensor output does not vary with the continuous use of the ammonia sensor 130. In a case shown in FIG. 3, the "Fresh" and the "Aged" have the same sensor output characteristics in the charge transfer resistance area.

The sensor output is degraded with the continuous use of the ammonia sensor 130 in the linear area. The degradation appears, in the linear area, as a decrease in slope of a straight line representing the sensor output characteristics. In the case shown in FIG. 3, the Aged one has a smaller slope of the straight line than the Fresh one.

In the ammonia sensor 130 which is the Aged one having been degraded as described above, use of the sensor output characteristics as it was set when the ammonia sensor 130 was the Fresh one is not preferable because an error occurs in concentration value calculated based on the sensor output value (the concentration value is calculated to be greater than an actual value).

To prevent such a problem, the sensor output characteristics in the linear area have to be reset, that is, calibration has to be performed at a predetermined timing at which the usage of the ammonia sensor 130 has been in progress.

In the present embodiment, the calibration is performed using a hydrocarbon gas (more specifically, a mixed atmosphere of carbon monoxide (CO) and total hydrocarbons (THC), hereinafter, also referred to as a CO+THC gas) for calibration formed by intentionally injecting a small amount of fuel from the fuel injection valves 301 for a short period of time.

This exploits the fact that the ammonia sensor 130, which is the mixed potential gas sensor having the above-mentioned configuration, has sensitivity not only for the ammonia gas but also for the CO+THC gas, and the sensor output characteristics of the ammonia sensor 130 for the CO+THC gas have a similar tendency to the sensor output characteristics for the ammonia gas. More specifically, the latter means that, when the sensor output characteristics of the ammonia sensor 130 for the CO+THC gas are plotted by taking the logarithmic value of a hydrocarbon gas concentration in the horizontal axis and taking the sensor output in the vertical axis as with the sensor output characteristics for the ammonia gas, the sensor output characteristics for the CO+THC gas are divided into the charge transfer resistance area and the linear area at the point A, and the variation with the use occurs only in the linear area, as shown in FIG. 3.

Generally speaking, the sensor output characteristics of the ammonia sensor 130 for the hydrocarbon gas are specified using the CO+THC gas beyond the oxidizing ability of the DOC 600 generated by an intentional injection of fuel from the fuel injection valves 301 both when the ammonia sensor 130 was the Fresh one and when the ammonia sensor 130 has become the Aged one with progress of its usage, and, based on a difference between the respective sensor output characteristics, the sensor output characteristics in the linear area of the Aged one for the ammonia gas are estimated. In this case, the hydrocarbon gas concentration is specified by detecting the hydrocarbon gas using the HC sensor 100. A fuel injection from the fuel injection valves 301 is performed as a post injection in an engine cycle of the engine main body 300.

Since the sensor output characteristics do not vary in the charge transfer resistance area as described above, in the charge transfer resistance area, the sensor output characteristics of the Fresh one can be used as the sensor output characteristics of the Aged one as they are. The calibration will be described in details below.

The fact that the ammonia sensor 130 has sensitivity also for the CO+THC gas means that, when the exhaust gas G including both the ammonia gas and the CO+THC gas flows to the location downstream from the SCR 800 at which the ammonia sensor 130 is located, an output from the ammonia sensor 130 is obtained by superimposing information on the ammonia gas and information on the CO+THC gas. In other words, a CO+THC gas component can interfere with the sensor output from the ammonia sensor 130. There is concern that the ammonia gas concentration cannot accurately be obtained if such interference is caused during normal operation of the engine system 1000, but, in this case, the CO+THC gas is almost entirely oxidized by the DOC 600 because the amount of fuel injected from the fuel injection valves 301 during the normal operation is smaller than that during the calibration. It can thus be said that almost no CO+THC gas is included in the exhaust gas G reaching the location downstream from the SCR 800 during the normal operation. There is no need to consider the interference of the CO+THC gas during the normal operation of the engine system 1000.

During the calibration, the supply of urea from the urea source 801 is suspended, and thus the ammonia gas does not cause interference when the sensor output characteristics for the CO+THC gas is obtained.

<Details of Calibration>

The calibration of the ammonia sensor 130 will be described in more details below. As described above, in the present embodiment, the sensor output characteristics in the linear area of the Aged one for the ammonia gas are estimated based on the sensor output characteristics for the CO+THC gas when the ammonia sensor 130 was the Fresh one and the sensor output characteristics for the CO+THC gas when the ammonia sensor 130 has become the Aged one with progress of its usage. This is based on the findings obtained by the inventors of the present invention that the relationships shown in the following equation (2) and inequations (3) hold, where $\Delta^f_{HC}$ and $\Delta^f_{NH}$ respectively denote a slope of the sensor output characteristics for the CO+THC gas and a slope of the sensor output characteristics for the ammonia gas when the ammonia sensor 130 is the Fresh one, and $\Delta^a_{HC}$ and $\Delta^a_{NH}$ respectively denote a slope of the sensor output characteristics for the CO+THC gas and a slope of the sensor output characteristics for the ammonia gas when the ammonia sensor 130 is the Aged one.

$$\Delta^f_{HC}/\Delta^f_{NH}=\Delta^a_{HC}/\Delta^a_{NH}=const. \quad (2)$$

$$\Delta^f_{HC}>\Delta^a_{HC} \text{ and } \Delta^f_{NH}>\Delta^a_{NH} \quad (3)$$

Figure 4A:
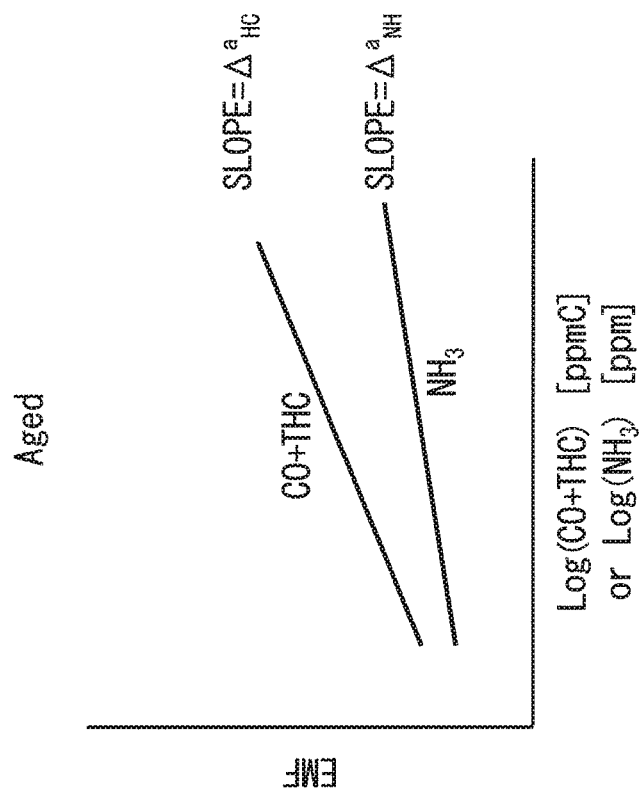
FIGS. 4A and 4B are each a schematic view of a linear area of sensor output characteristics for an ammonia gas and sensor output characteristics for a CO+THC gas.
Figure 4B:
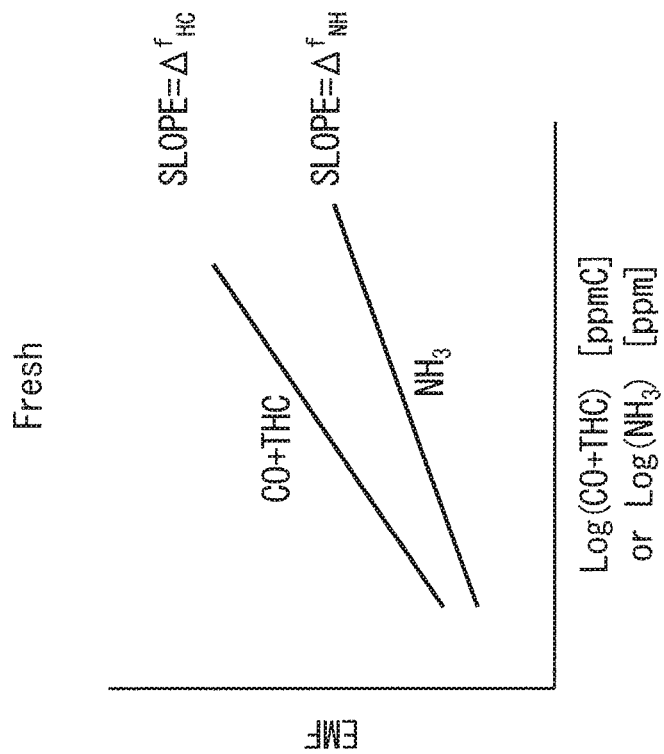

FIGS. 4A and 4B are each a schematic view of the linear area of the sensor output characteristics for the ammonia gas and the sensor output characteristics for the CO+THC gas, which correspond to the equation (2) and the inequations (3). FIG. 4A shows the linear area of the Fresh one, and FIG. 4B shows the linear area of the Aged one.

The equation (2) and the inequations (3) mean that, with the continuous use of the ammonia sensor 130, the sensor output characteristics for the CO+THC gas and the sensor output characteristics for the ammonia gas are degraded, and the slope of the sensor output characteristics for the CO+THC gas and the slope of the sensor output characteristics for the ammonia gas decrease, but the ratio of the slope of the sensor output characteristics for the CO+THC gas to the slope of the sensor output characteristics for the ammonia gas does not vary.

Thus, by specifying in advance the slope of the sensor output characteristics of the Fresh one for the CO+THC gas and the slope of the sensor output characteristics of the Fresh one for the ammonia gas, and specifying the slope of the sensor output characteristics of the Aged one for the CO+THC gas during the calibration, the slope of the sensor output characteristics of the Aged one for the ammonia gas can be obtained based on the following equation (4), which is a modification of the equation (2).

$$\Delta^a_{NH}=\Delta^a_{HC}/(\Delta^f_{HC}/\Delta^f_{NH}) \quad (4)$$

When the sensor output characteristics of the Aged one for the ammonia gas is updated using a value of the slope obtained as described above, the sensor output characteristics of the Aged one in line with a degradation state thereof can be obtained.

Figure 5:
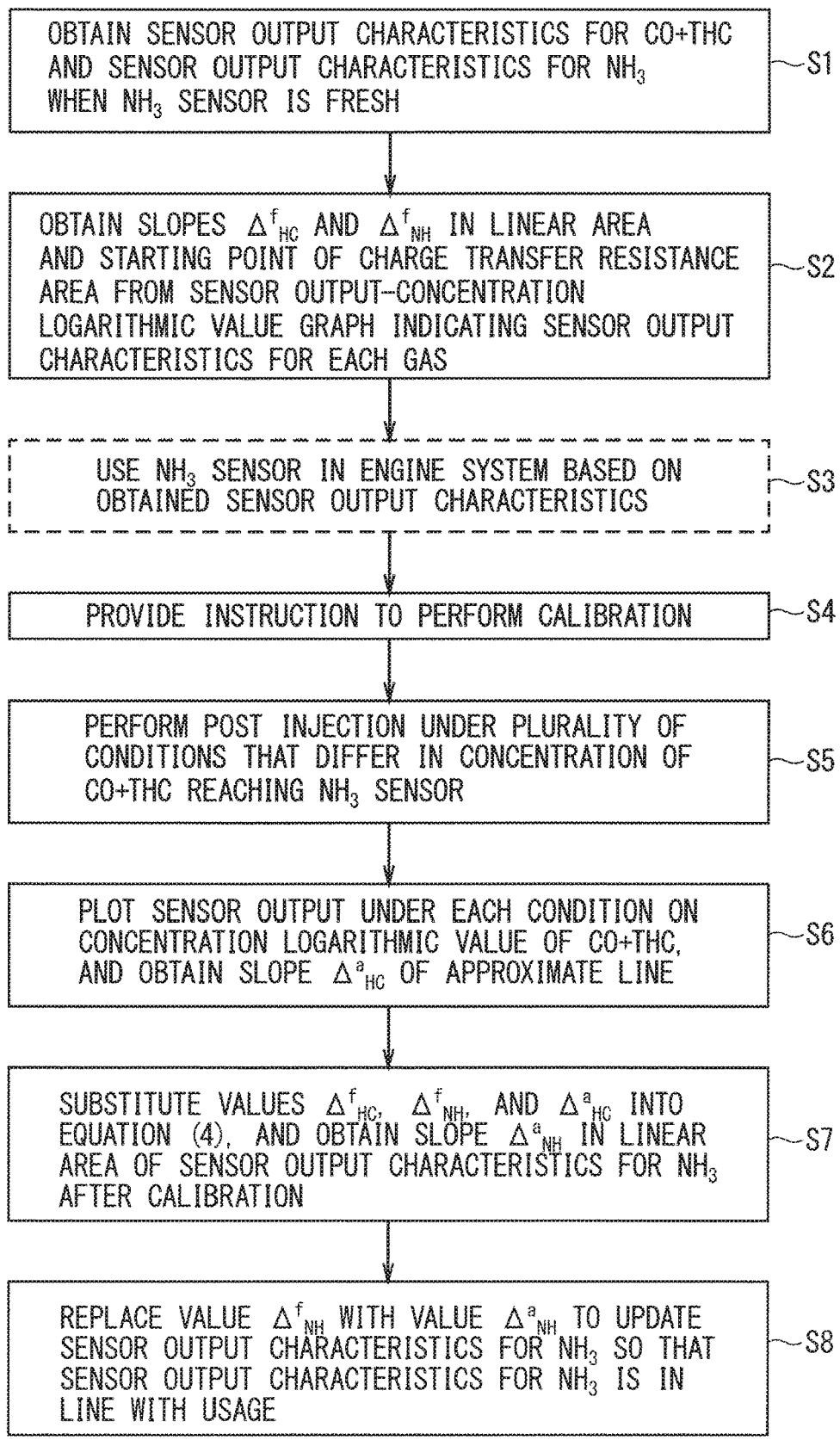
FIG. 5 shows specific procedures for performing calibration of the ammonia gas sensor 130.

FIG. 5 shows specific procedures for performing the calibration of the ammonia gas sensor 130. Prior to the use in the engine system 1000, the sensor output characteristics for the CO+THC gas and the sensor output characteristics for the ammonia gas when the ammonia sensor 130 is the Fresh one are obtained (step S1). As described above, the sensor output characteristics for the ammonia gas are experimentally specified by measuring the sensor output using, as the measurement gas, a plurality of different mixed gases having known ammonia gas concentrations, and are stored in the electronic controller 200. The sensor output characteristics for the CO+THC gas are obtained by performing similar processing. Alternatively, the sensor output characteristics for the CO+THC gas may be obtained by performing the above-mentioned post injection under a plurality of conditions that differ in concentration of the CO+THC gas reaching the ammonia sensor 130, in a state in which the ammonia sensor 130 is installed in the exhaust pipe 500 of the engine system 1000. In the case of the CO+THC gas, the concentration of a gas atmosphere providing the sensor output can be specified using the HC sensor 100 located upstream from the SCR 800, in contrast to the ammonia gas.

After the sensor output characteristics for the CO+THC gas and the sensor output characteristics for the ammonia gas are obtained, the slopes $\Delta^f_{HC}$ and $\Delta^f_{NH}$ in the linear area and the starting point A of the charge transfer resistance area are obtained from the sensor output-concentration logarithmic value graph indicating the sensor output characteristics for the CO+THC gas and the sensor output characteristics for the ammonia gas (step S2). The data is stored in the electronic controller 200.

The processing described so far is preparatory processing for the calibration of the ammonia sensor 130 performed prior to the use of the engine system 1000. The use of the engine system 1000 is hereinafter started under control performed by the electronic controller 200, and, in this case, the previously obtained sensitivity characteristics of the ammonia sensor 130 for the ammonia gas are used (step S3).

With the continuous use of the engine system 1000, the ammonia sensor 130 is degraded and then becomes the Aged one. An instruction to perform the calibration of the ammonia sensor 130 is provided to the engine system 1000 through an instruction means (not illustrated) (e.g., through operation of a predetermined switch of a vehicle when the engine system 1000 is mounted in the vehicle) at an appropriate timing (step S4). Alternatively, an operation program of the engine system 1000 may be set so that the calibration is performed automatically when a total time of use of the engine system 1000 from installation of the ammonia sensor 130 as a target of the calibration or a total traveling distance of the vehicle, in the case that the engine system 1000 is mounted in the vehicle, reaches a predetermined value.

In either case, the electronic controller 200 causes the fuel injection valves 301 to perform the post injection under the plurality of conditions that differ in concentration of the CO+THC gas reaching the ammonia sensor 130 in the phase of performing the calibration of the ammonia sensor 130 (step S5). In each case, the concentration of the CO+THC gas is specified using the HC sensor 100, and the sensor output from the ammonia sensor 130 is obtained. Furthermore, obtained values are plotted on sensor output-concentration logarithmic value coordinates, a slope of an approximate line of plotted data is obtained, and a value of the slope is determined as $\Delta^{a}_{HC}$ (step S6).

The oxygen concentration of the exhaust gas G when the post injection is performed is maintained preferably in a range of 12% to 21%. In this case, an error in sensor output value caused by the variation of the oxygen concentration is prevented or reduced.

After the value $\Delta^{a}_{HC}$ is obtained, the value $\Delta^{a}_{HC}$ is substituted into the equation (4) along with the values $\Delta^{f}_{HC}$ and $\Delta^{f}_{NH}$ specified in advance to calculate the value $\Delta^{a}_{NH}$ which comes to be treated as the slope in the linear area of the sensor output characteristics after the calibration for the ammonia sensor 130 being the Aged one (step S7).

After the value $\Delta^{a}_{NH}$ is obtained, the value $\Delta^{f}_{NH}$, which has been used as the slope of the sensor output characteristics so far, is replaced with the value $\Delta^{a}_{NH}$ to update the sensor output characteristics of the ammonia sensor 130 so that the sensor output characteristics are in line with usage so far (step S8). This prevents or reduces a decrease in accuracy of calculation of the ammonia gas concentration of the exhaust gas G, which is calculated based on the sensor output from the ammonia sensor 130.

Processing in and after step S5 may be performed again, if the need to perform the calibration again arises due to the progression of degradation of the ammonia sensor 130 with the continuous use of the engine system 1000.

As described above, according to the present embodiment, regarding to the ammonia sensor, which is located downstream from the SCR in the engine system, and has sensor output characteristics degraded with the continuous use of the engine system, the sensor output characteristics after degradation can suitably be specified based on the sensor output value obtained from the ammonia sensor itself. This means that the calibration of the ammonia sensor can be performed with high accuracy based on the output value from the ammonia sensor itself.

<Modifications>

In the above-mentioned embodiment, the calibration of the ammonia sensor 130 is performed using the sensor output characteristics of the Fresh one as a reference on the assumption that the equation (2) and the inequations (3) hold, and the calibration can be performed at the appropriate timing. It means that the values $\Delta^{a}_{HC}$ and $\Delta^{a}_{NH}$ of the slopes of the Aged one in the right-hand side of the equation (2) are values obtained at an appropriate timing. To amplify on this, the following equation and inequations hold, where $\Delta^{t1}_{HC}$ and $\Delta^{t2}_{HC}$ denote the value $\Delta^{a}_{HC}$ when times t1 and t2 (t1<t2) have elapsed since the start of use of the engine system 1000, and $\Delta^{t1}_{NH}$ and $\Delta^{t2}_{NH}$ denote the value $\Delta^{a}_{NH}$ when the times t1 and t2 have elapsed since the start of use of the engine system 1000 after installation of the ammonia sensor 130 as a target of the calibration.

$$\Delta^{f}_{HC}/\Delta^{f}_{NH} = \Delta^{t1}_{HC}/\Delta^{t1}_{NH} = \Delta^{t2}_{HC}/\Delta^{t2}_{NH} \tag{2a}$$

$$\Delta^{f}_{HC} > \Delta^{t1}_{HC} > \Delta^{t2}_{HC} \text{ and } \Delta^{f}_{NH} > \Delta^{t1}_{NH} > \Delta^{t2}_{NH} \tag{3a}$$

When the left-hand side is excluded from each of the equation (2a) and the inequations (3a), the following equation and inequations hold.

$$\Delta^{t1}_{HC}/\Delta^{t1}_{NH} = \Delta^{t2}_{HC}/\Delta^{t2}_{NH} \tag{2}$$

$$\Delta^{t1}_{HC} > \Delta^{t2}_{HC} \text{ and } \Delta^{t1}_{NH} > \Delta^{t2}_{NH} \tag{3a}$$

In view of the similarity of the equation (2b) and the inequations (3b) to the equation (2) and the inequations (3), the equation (2b) and the inequations (3b) indicate that, when the values $\Delta^{t1}_{HC}$ and $\Delta^{t1}_{NH}$ at the time t1 are specified in advance, and the value $\Delta^{t2}_{HC}$ can be specified at the time t2, the calibration can be performed at the time t2 using the values $\Delta^{t1}_{HC}$ and $\Delta^{t1}_{NH}$ at the time t1 as a reference, specifically, the value $\Delta^{t2}_{NH}$ can be specified based on the following equation (4b).

$$\Delta^{t2}_{NH} = \Delta^{t2}_{HC}/(\Delta^{t1}_{HC}/\Delta^{t1}_{NH}) \tag{4b}$$

This means that the sensor output characteristics of the Fresh one may not necessarily be used as a reference when the above-mentioned calibration of the ammonia sensor 130 is performed. In other words, it can be said that the sensor output characteristics of the Fresh one are used as a reference only in a particular case in which the time t1 is 0 in the equation (4b).

Based on the equation (4b), when the calibration is performed again after the elapse of further time after the calibration is performed once, for example, the sensor output characteristics updated in the previous calibration can be used as a reference instead of using the sensor output characteristics of the Fresh one as a reference.

In the above-mentioned embodiment, the concentration of the CO+THC gas reaching the ammonia sensor 130 in the calibration is obtained, so to say, directly using the HC sensor 100, but the concentration of the CO+THC gas may not necessarily be obtained directly. For example, the concentration of the CO+THC gas may be estimated indirectly using a technique of evaluating the oxidizing ability of the DOC 600. For example, the concentration of the CO−THC gas may be estimated using a ΔT method in which the temperature at the location upstream from the DOC 600 and the temperature at the location downstream from the DOC 600 are measured using a thermocouple, and the oxidizing ability is estimated based on a difference therebetween, or may be estimated using a NO/NO$_2$ conversion efficiency specified by a multi-gas sensor that can simultaneously detect NOx and NO$_2$.

EXAMPLES

Example 1

(Confirmation of Sensor Output Characteristics)

The sensor output for each of the CO+THC gas and the ammonia gas was obtained for six ammonia sensors 130 (No. 1 to No. 6) having different combinations of a porosity of the surface protective layer 50 of the sensor element 131 and an operation time of the engine main body 300 (hereinafter, an engine operation time) from installation in the exhaust pipe 500. The porosity of the surface protective layer 50 was at two different levels of 12% and 40%. On the other hand, the engine operation time was at three different levels of 0 h (hours), 2000 h, and 4000 h. When the engine main body 300 is operated, installation of the DOC 600, the DPF 700, and the SCR 800 in the exhaust pipe 500 was omitted, and a FID analyzer for obtaining the concentration of the CO+THC gas was installed in the exhaust pipe 500 instead. The operation was a cycle operation in which 30 minutes constitute one cycle.

The combinations of the porosity of the surface protective layer 50 and the engine operation time for each ammonia sensor 130 are shown in Table 1.

TABLE 1

| SENSOR | PROTECTIVE LAYER POROSITY (%) | ENGINE OPERATION TIME (h) |
|---|---|---|
| No. 1 | 12 | 0 |
| No. 2 | 12 | 2000 |
| No. 3 | 12 | 4000 |
| No. 4 | 40 | 0 |
| No. 5 | 40 | 2000 |
| No. 6 | 40 | 4000 |

A driving temperature of the sensor element 131 in the ammonia sensor 130 was set to 500°, and the detection electrode 10 and the reference electrode 20 were held at the same temperature.

The sensor output characteristics for the CO+THC gas were specified by obtaining the output from the ammonia sensor 130 and the measured value from the FID analyzer repeatedly for a predetermined time period in a state in which the ammonia sensor 130 was installed in the exhaust pipe 500, and the engine main body 300 was operated.

On the other hand, the sensor output characteristics for the ammonia gas were specified by, installing the ammonia sensor in a model gas apparatus, and obtaining the sensor output in a state that an ammonia gas-containing atmosphere having a known concentration was generated in the model gas apparatus. This was performed before installation in the exhaust pipe 500 in the case of the Fresh one and after the elapse of the operation time shown in Table 1 in the case of the Aged one. Conditions in this case were as follows:

Gas temperature: 120° C.;
Gas flow rate: 200 L/min; and
Gas species and concentration: NH$_3$=1 ppm, 5 ppm, 10 ppm, 25 ppm, 50 ppm, 100 ppm, 300 ppm, 500 ppm, 750 ppm, or 1000 μm, O$_2$=10%, H$_2$O=5%, and N$_2$=balance.

Figure 6A:
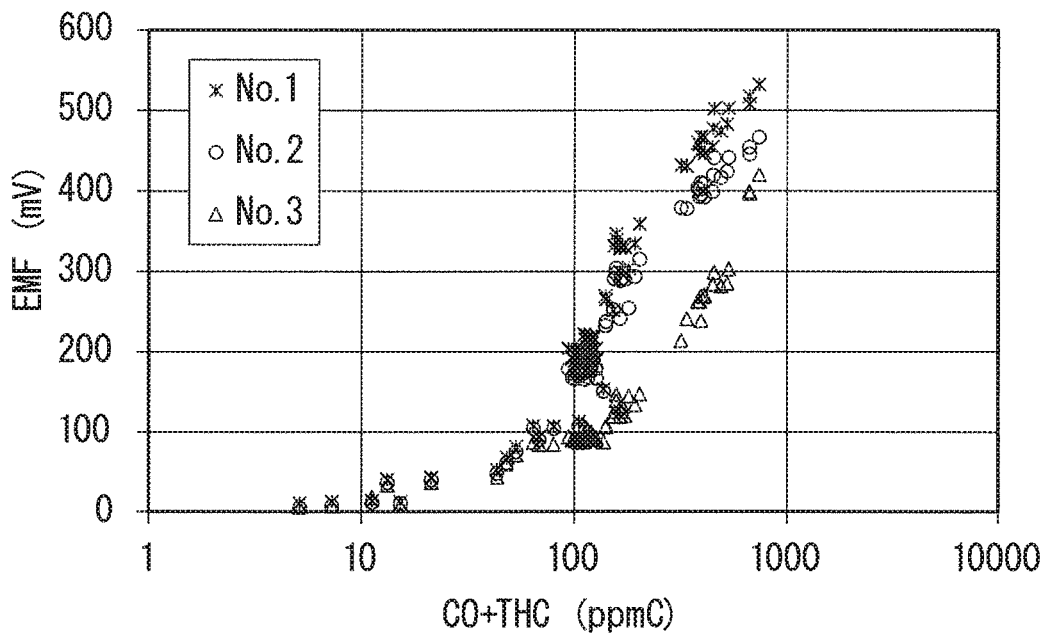
FIGS. 6A and 6B each show the sensor output characteristics for the CO+THC gas.
Figure 6B:
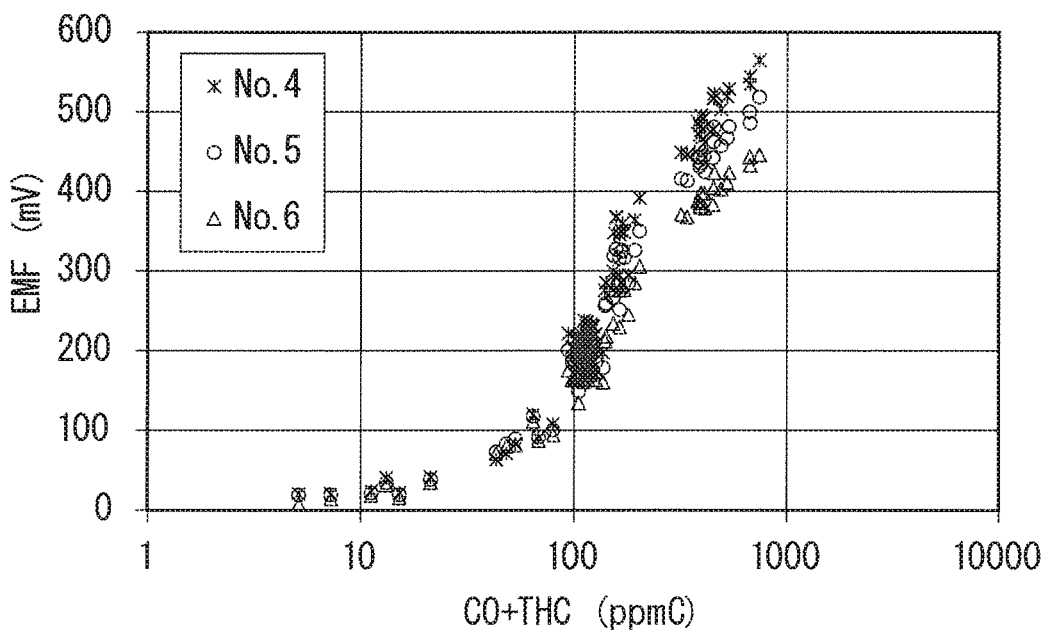

FIGS. 6A and 6B each show the sensor output characteristics (sensor output-concentration logarithmic value graph) for the CO+THC gas. FIG. 6A shows the sensor output characteristics for No. 1 to No. 3 of the ammonia sensors 130, and FIG. 6B shows the sensor output characteristics for No. 4 to No. 6 of the ammonia sensors 130.

It is confirmed from FIGS. 6A and 6B that, in each of No. 1 to No. 6 of the ammonia sensors 130, the sensor output (EMF) varies linearly with the concentration logarithmic value in a range of the sensor output of approximately 100 mV or more, although they differ in concentration value itself. It is thus determined that, in the sensor output characteristics for No. 1 to No. 6 of the ammonia sensors 130 for the CO+THC gas, at least the range of the sensor output (EMF) of 100 mV or more corresponds to the linear area. In this case, a range of the sensor output (EMF) of less than 100 mV corresponds to the charge transfer resistance area.

Figure 7A:
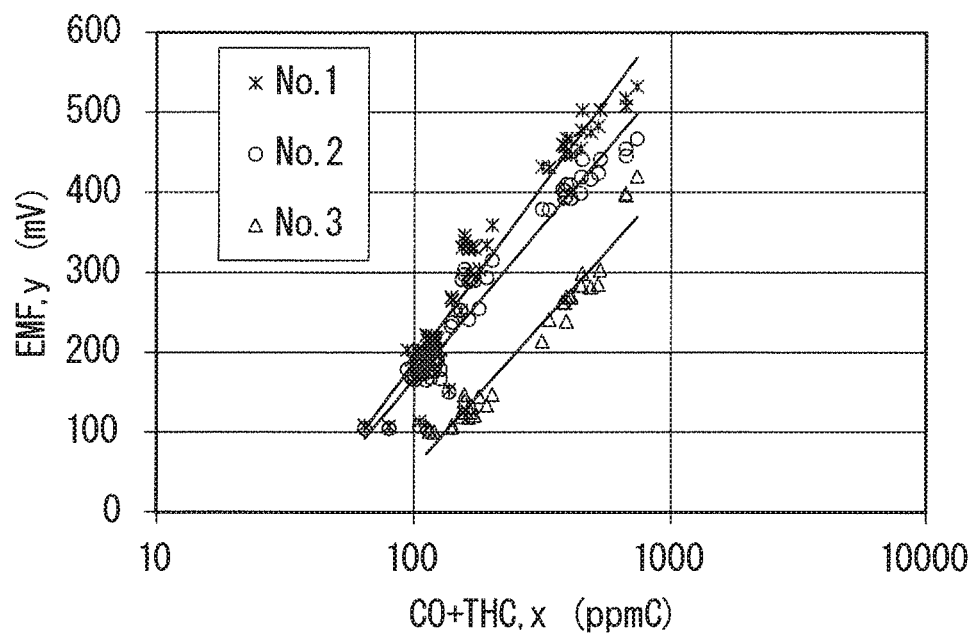
FIGS. 7A and 7B show data in a range of a sensor output of 100 mV or more in FIGS. 6A and 6B, together with approximate lines as obtained.
Figure 7B:
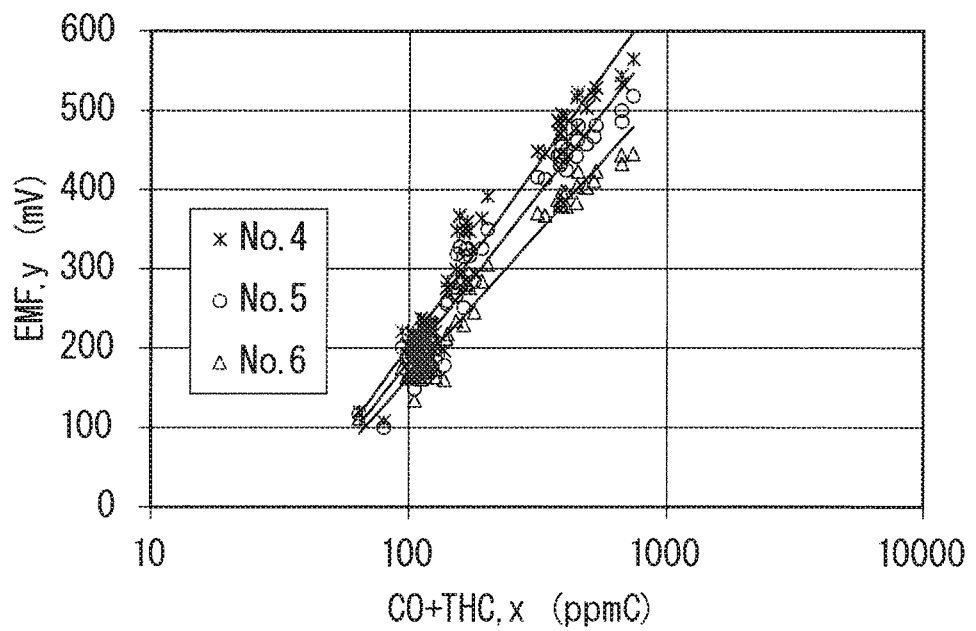

In view of this, an equation representing the approximate line in the linear area was specified for each of No. 1 to No. 6 of the ammonia sensors 130 using only data when the sensor output (EMF) is 100 mV or more. Specifically, with respect to the data, a value of a slope a and a value of an intercept b of an equation y=a·log$_{10}$(x)+b representing the approximate line, in which x denotes the concentration of the CO+THC gas and y denotes the sensor output, were obtained using a least-squares method. The obtained value of the slope a of the approximate line is shown as $\Delta_{HC}$ in Table 2 shown below. FIGS. 7A and 7B show data in the range of the sensor output (EMF) of 100 mV or more in FIGS. 6A and 6B, together with approximate lines as obtained. FIG. 7A shows the data for No. 1 to No. 3 of the ammonia sensors 130, and FIG. 7B shows the data for No. 4 to No. 6 of the ammonia sensors 130.

A square value (a coefficient of determination) $R^2$ of a correlation coefficient R of each approximate line is in a range of 0.94 to 0.96. It is thus determined that the sensor output characteristics for the CO+THC gas actually have good linearity in the linear area.

Figure 8A:
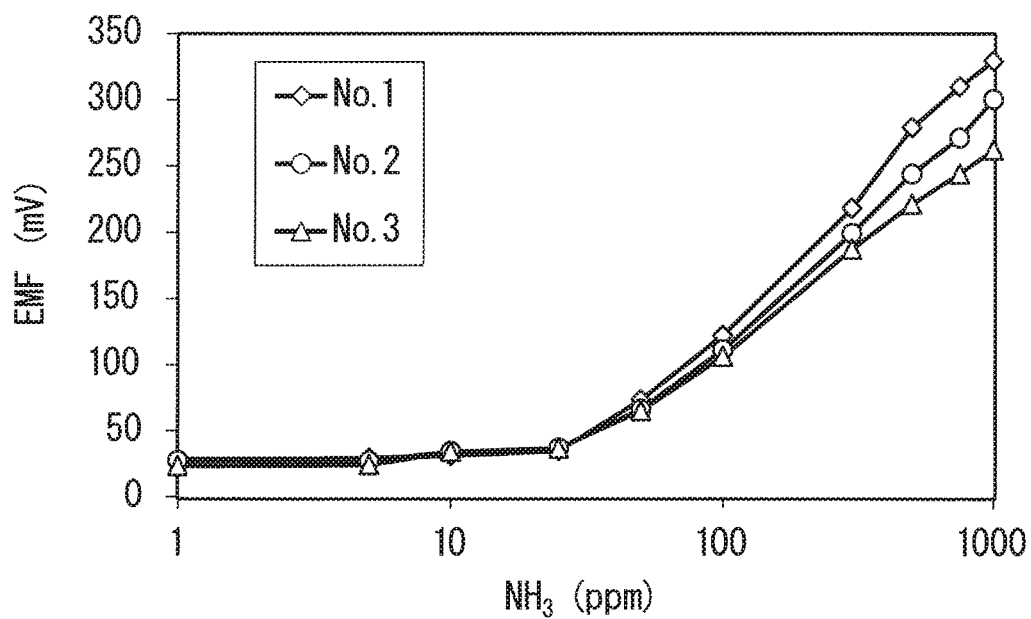
FIGS. 8A and 8B each show the sensor output characteristics for the ammonia gas.
Figure 8B:
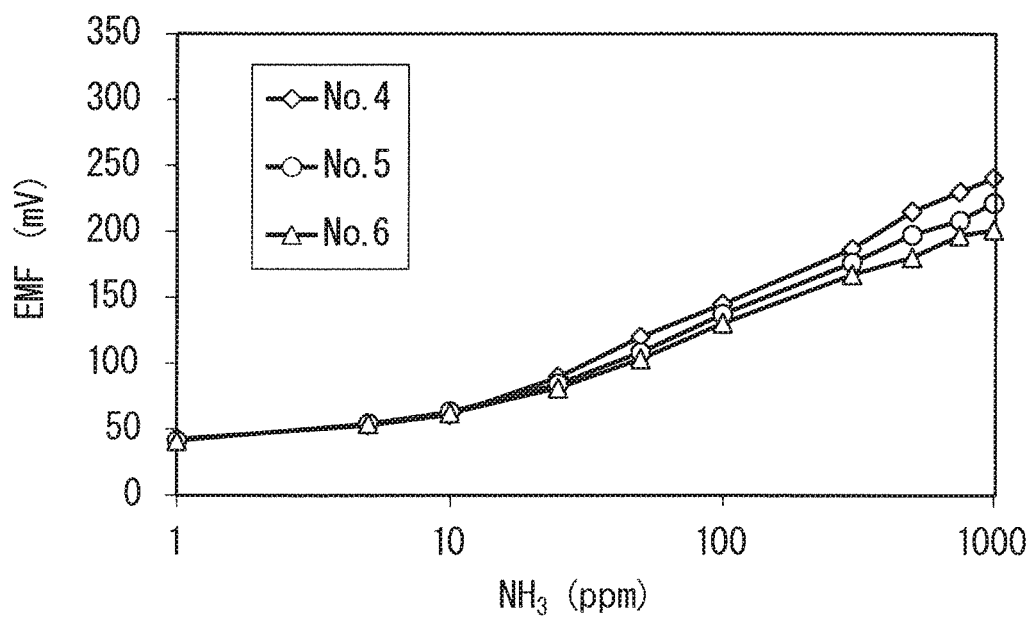

On the other hand, FIGS. 8A and 8B each show the sensor output characteristics (sensor output-concentration logarithmic value graph) for the ammonia gas. FIG. 8A shows the sensor output characteristics for No. 1 to No. 3 of the ammonia sensors 130, and FIG. 8B shows the sensor output characteristics for No. 4 to No. 6 of the ammonia sensors 130.

It is confirmed from FIGS. 8A and 8B that the sensor output varies linearly with the concentration logarithmic value at least in a range of the ammonia gas concentration of 50 ppm or more in each of No. 1 to No. 3 of the ammonia sensors 130, and at least in a range of the ammonia gas concentration of 25 ppm or more in each of No. 4 to No. 6 of the ammonia sensors 130. These ranges are each determined to correspond to the linear area of the sensor output characteristics of the ammonia sensors 130 for the ammonia gas. In this case, a range of the ammonia gas concentration of less than 50 ppm corresponds to the charge transfer resistance area for each of No. 1 to No. 3 of the ammonia sensors 130, and a range of the ammonia gas concentration of less than 25 ppm corresponds to the charge transfer resistance area for each of No. 4 to No. 6 of the ammonia sensors 130.

Figure 9A:
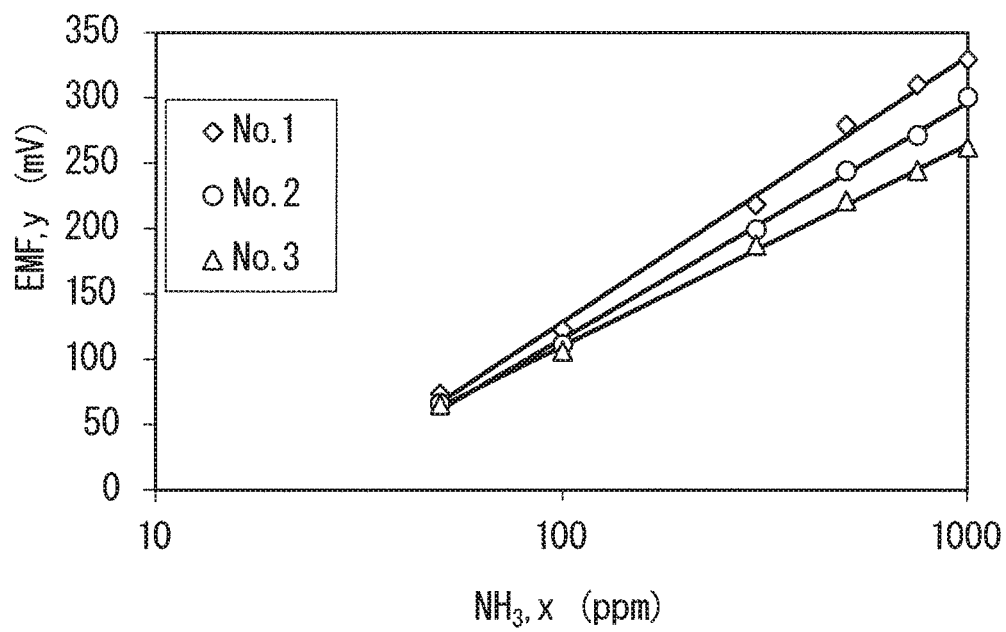
FIGS. 9A and 9B show data belonging to the linear area in FIGS. 8A and 8B, together with approximate lines in the linear area.
Figure 9B:
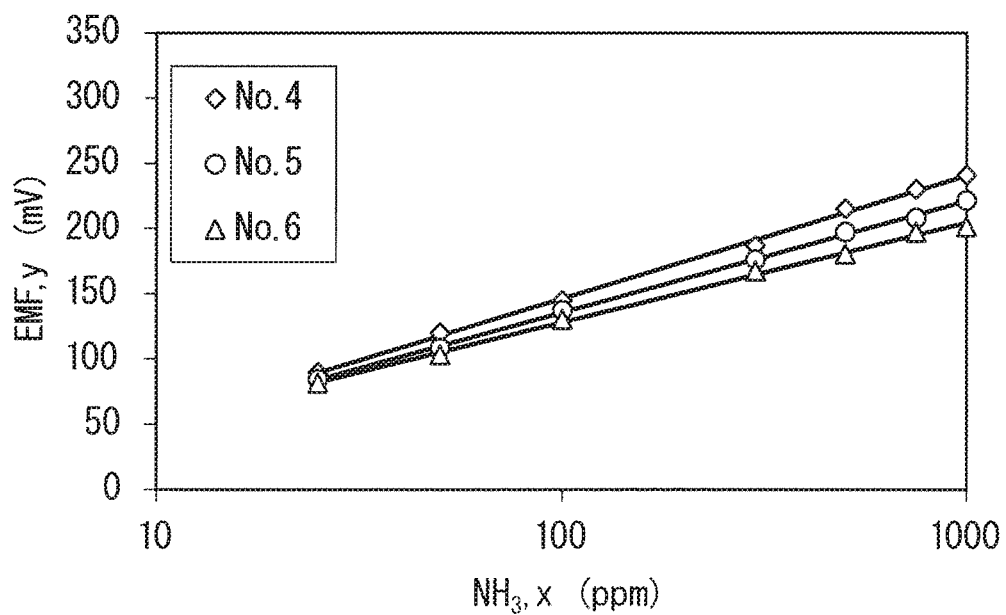

In view of this, an equation representing the approximate line in the linear area was specified for each of No. 1 to No. 3 of the ammonia sensors 130 using only data when the ammonia gas concentration is in the range of 50 ppm or more, and for each of No. 4 to No. 6 of the ammonia sensors 130 using only data when the ammonia gas concentration is in the range of 25 ppm or more, as in the case of the CO+THC gas. The obtained value of the slope of the approximate line is shown as $\Delta_{NH}$ in Table 2. FIGS. 9A and 9B show data belonging to the linear area in FIGS. 8A and 8B, together with approximate lines as obtained. FIG. 9A shows the data of No. 1 to No. 3 of the ammonia sensors 130, and FIG. 9B shows the data of No. 4 to No. 6 of the ammonia sensors 130.

The square value (coefficient of determination) $R^2$ of the correlation coefficient R of each approximate line is in a range of 0.995 to 0.999, which is extremely close to one. It is thus determined that the sensor output characteristics for the ammonia gas actually have good linearity in the linear area.

TABLE 2

| | SLOPE OF APPROXIMATE LINE IN LINEAR AREA | | |
| --- | --- | --- | --- |
| | CO + THC ($\Delta_{HC}$) | $NH_3$ ($\Delta_{NH}$) | RATIO OF SLOPE ($\Delta_{HC}/\Delta_{NH}$) |
| No. 1 | 439.24 | 191.94 | 2.3 |
| No. 2 | 382.80 | 180.43 | 2.1 |
| No. 3 | 360.72 | 154.25 | 2.3 |
| No. 4 | 455.70 | 94.36 | 4.8 |
| No. 5 | 418.20 | 85.49 | 4.9 |
| No. 6 | 364.55 | 76.45 | 4.8 |

It is confirmed from Table 2 that, when values of the slope $\Delta_{HC}$ and values of the slope $\Delta_{NH}$ are each compared among No. 1 to No. 3 of the ammonia sensors 130, which has the same porosity (configuration) in the surface protective layer 50, and among No. 4 to No. 6 of the ammonia sensors 130, which has the same porosity (configuration) in the surface protective layer 50, the values tend to decrease with increasing engine operation time. This means that the sensor output characteristics (in the linear area) for each gas species are degraded with the continuous use of the ammonia sensor 130.

<Calibration>

Table 2 also shows results of calculation of a ratio $\Delta_{HC}/\Delta_{NH}$ of the value $\Delta_{HC}$ to the value $\Delta_{NH}$ for each of No. 1 to No. 6 of the ammonia sensors 130. The value of the ratio $\Delta_{HC}/\Delta_{NH}$ is 2.1 or 2.3 for No. 1 to No. 3 of the ammonia sensors 130, and is 4.8 or 4.9 for No. 4 to No. 6 of the ammonia sensors 130. That is to say, values of the ratio $\Delta_{HC}/\Delta_{NH}$ of the ammonia sensors 130 having the same porosity (configuration) of the surface protective layer 50 are approximately equal to each other.

The sensors No. 1 and No. 4 among the above ammonia sensors 130 whose engine operation time is zero herein correspond to Fresh ones having different configurations each other. On the other hand, the sensors No. 2 and No. 3 among the above ammonia sensors 130 that differ from the sensor No. 1 only in the engine operation time are understood as Aged ones corresponding to the sensor No. 1. The sensors No. 5 and No. 6 among the above ammonia sensors 130 that differ from the sensor No. 4 only in the engine operation time are Aged ones corresponding to the sensor No. 4.

The results shown in Table 2 can thus be considered to indicate that a Fresh one and an Aged one have different sensor output characteristics themselves, but the value of the ratio $\Delta_{HC}/\Delta_{NH}$ of the slope of the sensor output characteristics is maintained even when the engine operation time increases. This means that the relationship shown in the above-mentioned equation (2) holds.

Specifically, in Table 2, the value of the ratio $\Delta_{HC}/\Delta_{NH}$ for each of the sensors No. 1 and No. 4 corresponding to the Fresh ones corresponds to the value $\Delta^f_{HC}/\Delta^f_{NH}$ in the equation (2), and the value of the ratio $\Delta_{HC}/\Delta_{NH}$ for each of the sensors No. 2, No. 3, No. 5, and No. 6 corresponding to the Aged ones corresponds to the value $\Delta^a_{HC}/\Delta^a_{NH}$ in the equation (2).

Pseudo-calibration (correction of the sensor output characteristics) was performed using the ratio $\Delta_{HC}/\Delta_{NH}$ for the sensor No. 1 and the value $\Delta_{HC}$ for each of the sensors No. 2 and No. 3 on the assumption that the sensors No. 2 and No. 3 were actually the Aged ones for the sensor No. 1. Similarly, pseudo-calibration was performed using the ratio $\Delta_{HC}/\Delta_{NH}$ for the sensor No. 4 and the value $\Delta_{HC}$ for each of the sensors No. 5 and No. 6 on the assumption that the sensors No. 5 and No. 6 were actually the Aged ones for the sensor No. 4.

Specifically, as for the charge transfer resistance area, the charge transfer resistance area of the sensor output characteristics of each of the sensors No. 1 and No. 4 was used as it is.

On the other hand, as for the linear area, the value of the slope $\Delta^a_{NH}$ in the linear area of each of the sensors No. 2 and No. 3 was calculated from the value $\Delta_{HC}$ for each of the sensors No. 2 and No. 3 and the value of the ratio $\Delta_{HC}/\Delta_{NH}$ of the sensor No. 1 using the equation (4), which is based on the fact that the value $\Delta_{HC}$ for each of the sensors No. 2 and No. 3 corresponds to the slope $\Delta^a_{HC}$ of the sensor output of each of the Aged ones for the sensor No. 1 that differ from each other in degree of degradation. Similarly, the value of the slope $\Delta^a_{NH}$ in the linear area of each of the sensors No. 5 and No. 6 was calculated from the value $\Delta_{HC}$ for each of the sensors No. 5 and No. 6 and the value of the ratio $\Delta_{HC}/\Delta_{NH}$ of the sensor No. 4 using the equation (4), which is based on the fact that the value $\Delta_{HC}$ of each of the sensors No. 5 and No. 6 corresponds to the slope $\Delta^a_{HC}$ of the sensor output of each of the Aged ones for the sensor No. 4 that differ from each other in degree of degradation.

A range, of a straight line whose slope has the calculated value $\Delta^a_{NH}$, in which the concentration value is equal to or higher than the concentration value at the starting point of the charge transfer resistance area indicates the sensor output characteristics in the linear area after the calibration.

FIGS. 10A, 10B, 11A, and 11B respectively show results of the (pseudo-)calibration of the sensors No. 2, No. 3, No. 5, and No. 6. Specifically, graphs indicated in solid lines in FIGS. 10A, 10B, 11A, and 11B respectively show the results of the calibration (the sensor output characteristics after pseudo-correction) of the sensors No. 2, No. 3, No. 5, and No. 6. In each of FIGS. 10A, 10B, 11A, and 11B, the sensor output characteristics (being the same as those shown in FIGS. 8A, 8B, 9A, and 9B) of the corresponding ammonia sensor 130 obtained by actual measurement are indicated in an alternate long and short dashed line, and the sensor output characteristics (being the same as those shown in FIGS. 8A, 8B, 9A, and 9B) of the sensor No. 1 or No. 4 obtained by actual measurement are indicated in a broken line for comparison.

It is confirmed from FIGS. 10A, 10B, 11A, and 11B that the sensor output characteristics obtained by the calibration almost suitably match the sensor output characteristics of the corresponding ammonia sensor 130 obtained by actual measurement.

Figure 11A:
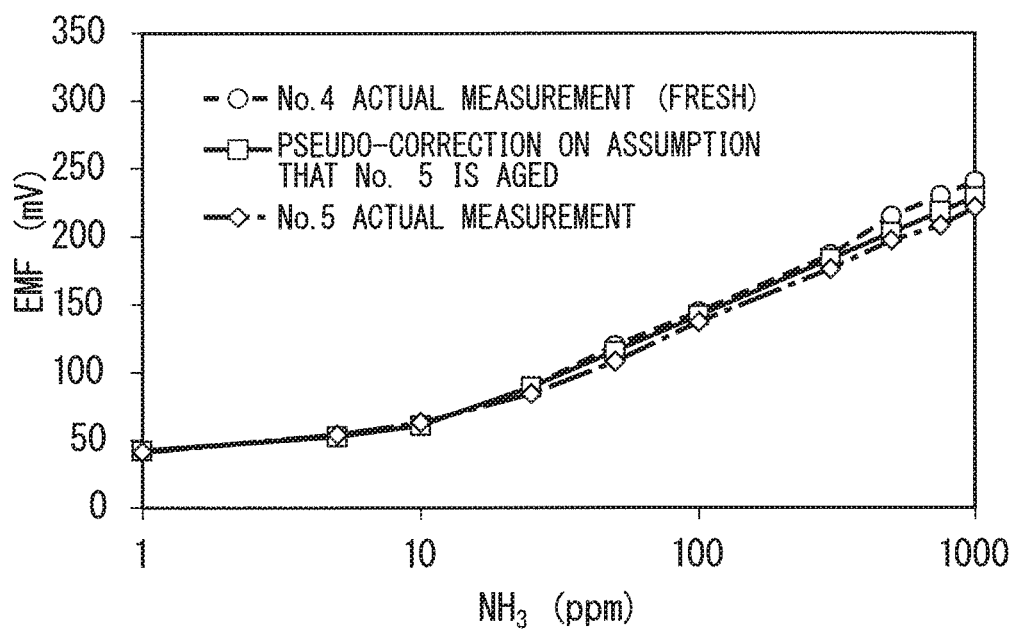
FIG. 11A shows a result of calibration of an ammonia sensor No. 5.
Figure 11B:
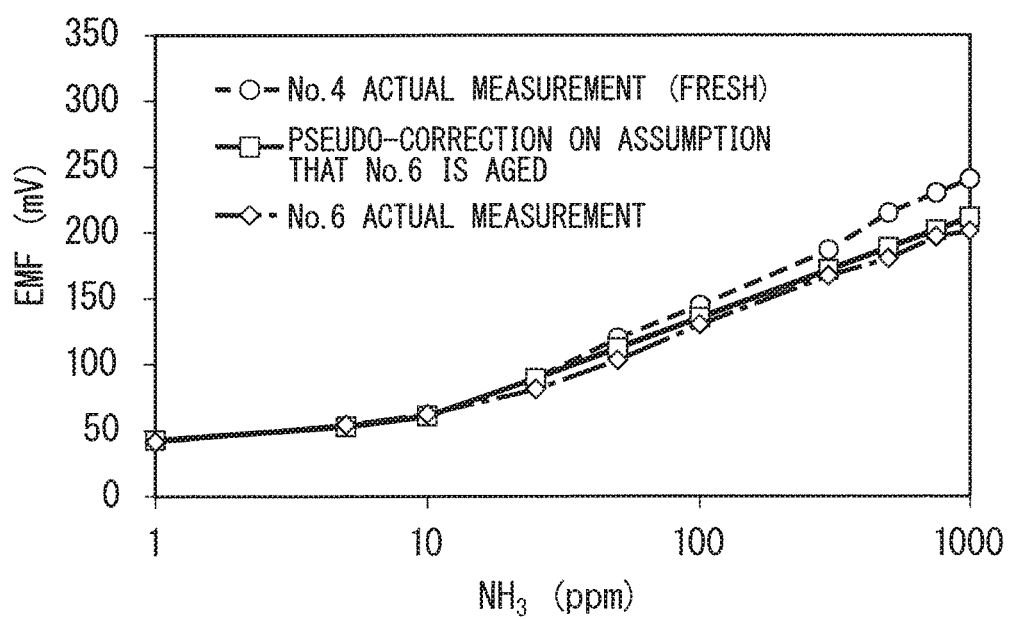
FIG. 11B shows a result of calibration of an ammonia sensor No. 6.

In particular, in a relatively high concentration range of 500 ppm or more, a gap between the sensor output characteristics of the Fresh one (No. 1 or No. 4) and the sensor output characteristics of the Aged one (No. 2, No. 3, or No. 6) is relatively large except for the results of the ammonia sensor 130 No. 5 shown in FIG. 11A, but the gap is approximately eliminated in the sensor output characteristics obtained by the calibration.

The results indicate that the calibration based on the equation (4) is effective.

Example 2

In Example 1, in obtaining the sensor output characteristics for the CO+THC gas, installation of the DOC 600, the DPF 700, and the SCR 800 in the exhaust pipe 500 was omitted to allow the exhaust gas G from the engine to directly reach the ammonia sensor 130, and the concentration of the CO+THC gas was measured using the specially attached FID analyzer to obtain many data points having different concentrations of the CO+THC gas. In this case, not only the concentration of the CO+THC gas but also the oxygen concentration varies in the exhaust gas G, but it is known that the oxygen concentration is an error factor when the sensor output for the CO+THC gas is obtained.

In the case that the calibration of the ammonia sensor 130 becoming the Aged one with the continuous use of the engine system 1000 is actually performed with the aged ammonia sensor 130 being installed in the exhaust pipe 500, the CO+THC gases having different concentrations are generated by performing the post injection as described above during an interval between normal operations in order to obtain the sensor output characteristics of the aged ammonia sensor 130, and, in this case, the number of data pieces used to specify the sensor output characteristics might be smaller than that in Example 1.

In Example 1, the effect of the error in sensor output value caused by the oxygen concentration is eventually prevented or reduced by obtaining many data pieces, but, when the number of obtained data pieces is small, the error in sensor output value caused by the variation of the oxygen concentration is relatively large, and the sensor output characteristics obtained using such a sensor output value are likely to include the error. It is thus desirable to limit a range of the oxygen concentration of the exhaust gas G at the post injection in advance when the sensor output characteristics are obtained by performing the post injection.

In view of the above-mentioned point, in the present example, the above-mentioned pseudo-calibration is performed again using only data having an oxygen concentration calculated using the output from the oxygen sensor 120 of 12% to 21% from data used to obtain the sensor output characteristics for the CO+THC gas in Example 1, so as to confirm the effect of limiting the oxygen concentration.

Figure 12A:
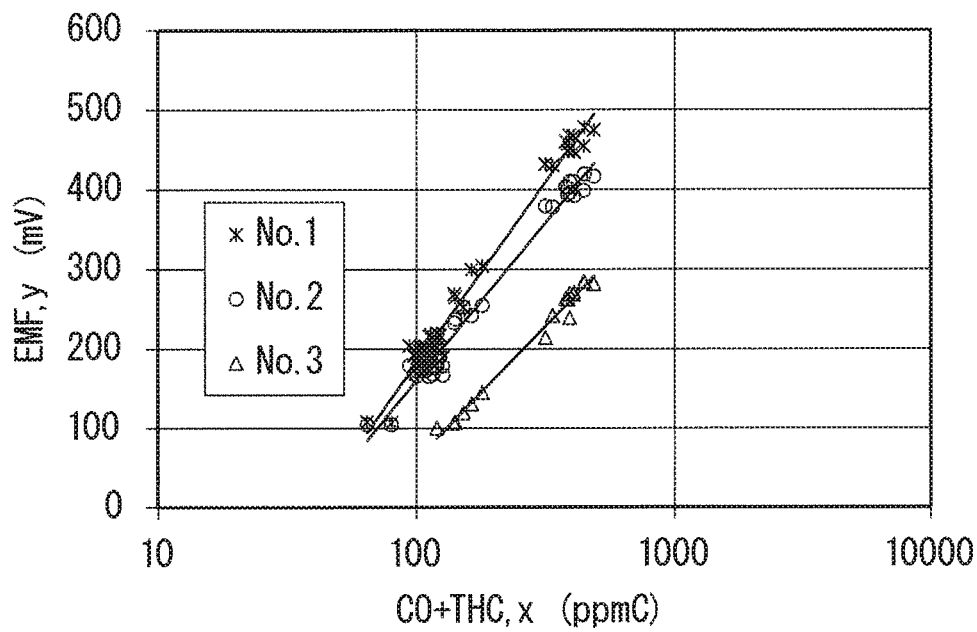
FIGS. 12A and 12B show data having an oxygen concentration of an exhaust gas G of 12% to 21% in FIGS. 7A and 7B, together with approximate lines in the linear area.
Figure 12B:
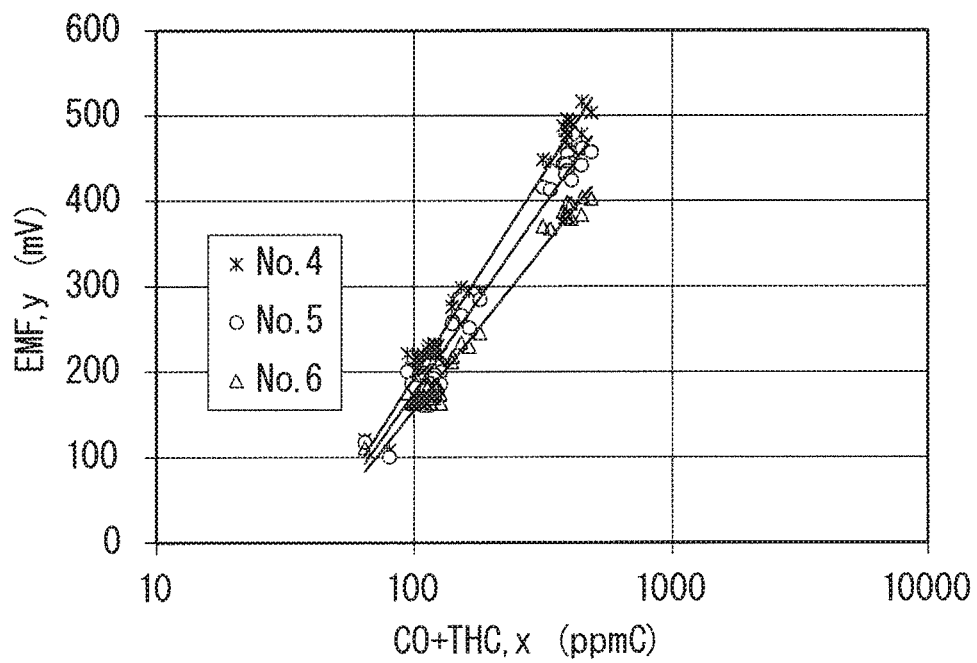
Figure 14A:
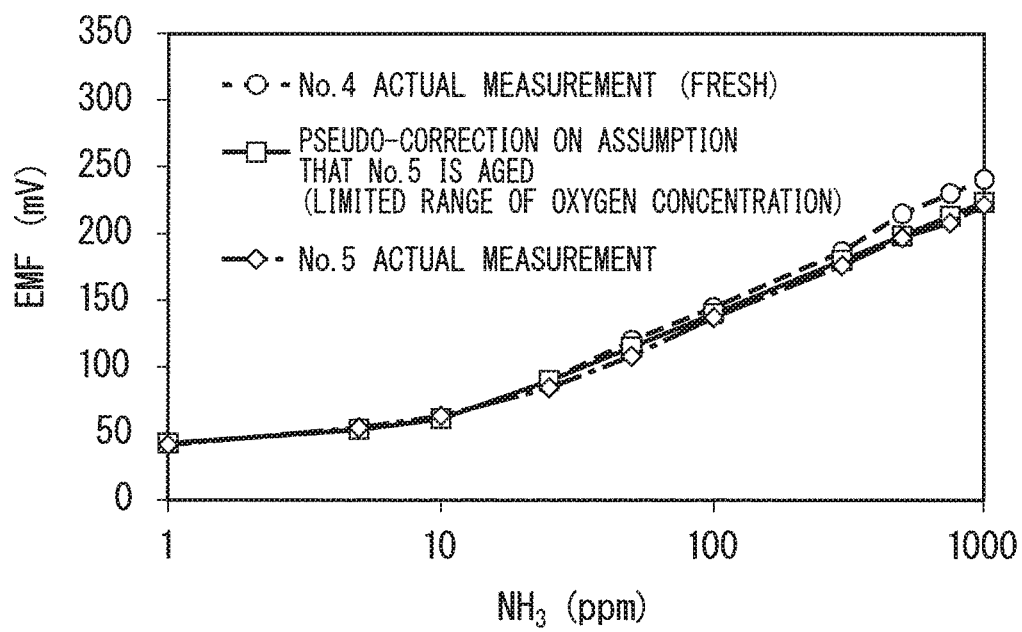
FIG. 14A shows a result of calibration of the ammonia sensor No. 5.
Figure 14B:
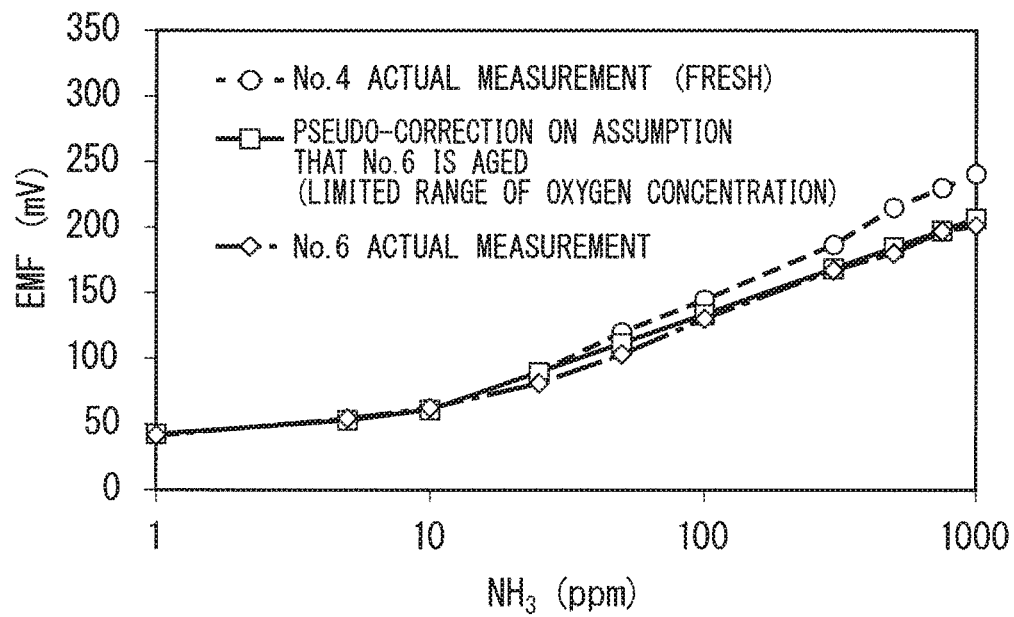
FIG. 14B shows a result of calibration of the ammonia sensor No. 6.

Specifically, the equation representing the approximate line in the linear area of the sensor output characteristics for the CO+THC gas shown in FIGS. 6A and 6B was specified again using only data having an oxygen concentration of the exhaust gas G of 12% to 21% from data used in FIGS. 7A and 7B. FIGS. 12A and 12B show the data, together with approximate lines as obtained. FIG. 12A shows the data of the sensors No. 1 to No. 3, and FIG. 12B shows the data of the sensors No. 4 to No. 6.

The square value (coefficient of determination) $R^2$ of the correlation coefficient R of each approximate line is in a range of 0.98 to 0.99, which is closer to one than the value relating to the approximate lines shown in FIGS. 7A and 7B. It can thus be said that the sensor output characteristics for the CO+THC gas obtained again in the present example have better linearity in the linear area than those obtained in Example 1.

The value $\Delta_{HC}$ of the slope of the approximate line shown in FIGS. 12A and 12B is shown in Table 3 along with the value $\Delta_{NH}$ relating to the ammonia gas shown in Table 2. Table 3 further shows the result of calculation of the ratio $\Delta_{HC}/\Delta_{NH}$ of the value $\Delta_{HC}$ to the value $\Delta_{NH}$.

TABLE 3

| | SLOPE OF APPROXIMATE LINE IN LINEAR AREA | | |
|---|---|---|---|
| | CO + THC ($\Delta_{HC}$) | NH$_3$ ($\Delta_{NH}$) | RATIO OF SLOPE ($\Delta_{HC}/\Delta_{NH}$) |
| No. 1 | 454.28 | 191.94 | 2.4 |
| No. 2 | 395.70 | 180.43 | 2.2 |
| No. 3 | 335.10 | 154.25 | 2.2 |
| No. 4 | 473.96 | 94.36 | 5.0 |
| No. 5 | 433.88 | 85.49 | 5.1 |
| No. 6 | 378.73 | 76.46 | 5.0 |

It is confirmed that the value $\Delta_{HC}$ of the slope shown in Table 3 tends to decrease with increasing engine operation time, as in the case of Table 2.

The value of the ratio $\Delta_{HC}/\Delta_{NH}$ is 2.4 or 2.2 for the sensors No. 1 to No. 3, and is 5.0 or 5.1 for the sensors No. 4 to No. 6. That is to say, values of the ratio $\Delta_{HC}/\Delta_{NH}$ of the ammonia sensors 130 having the same porosity (configuration) of the surface protective layer 50 are approximately equal to each other also in the present example.

In the present example, pseudo-calibration was performed by the processing similar to the processing performed in Example 1, on the assumption that the sensors No. 2 and No. 3 were actually the Aged ones for the sensor No. 1 and the sensors No. 5 and No. 6 were actually the Aged ones for the sensor No. 4.

FIGS. 13A, 13B, 14A, and 14B respectively show results of the (pseudo-)calibration of the sensors No. 2, No. 3, No. 5, and No. 6. Specifically, graphs indicated in solid lines in FIGS. 13A, 13B, 14A, and 14B respectively show the results of the calibration of the sensors No. 2, No. 3, No. 5, and No. 6. In the present example, the sensor output characteristics of the corresponding ammonia sensor 130 obtained by actual measurement are indicated in an alternate long and short dashed line, and the sensor output characteristics of the sensor No. 1 or No. 4 obtained by actual measurement are indicated in a broken line for comparison.

Figure 10A:
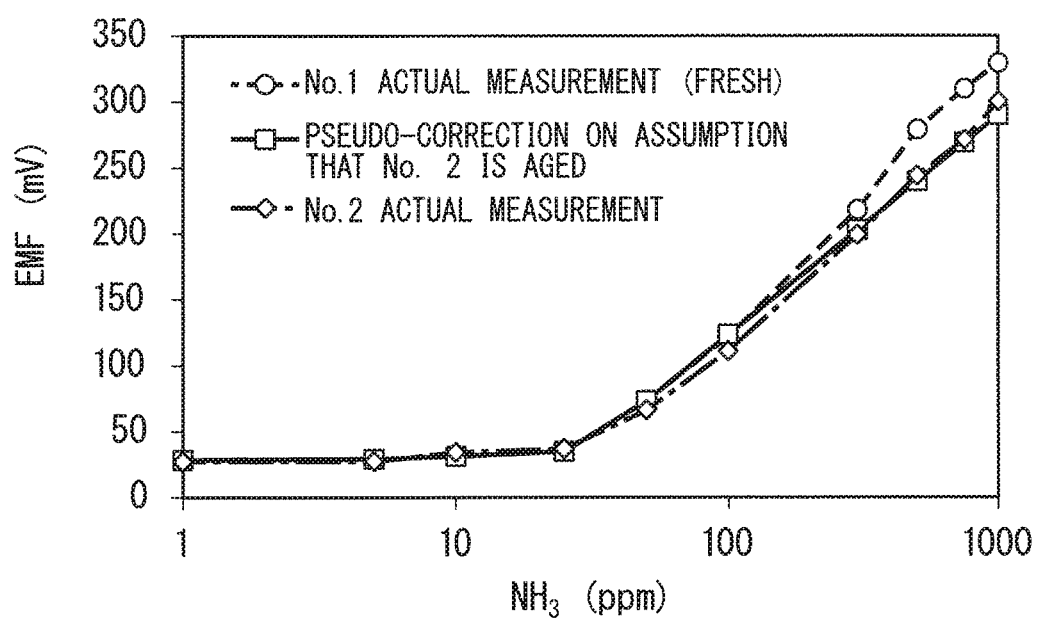
FIG. 10A shows a result of calibration of an ammonia sensor No. 2.
Figure 10B:
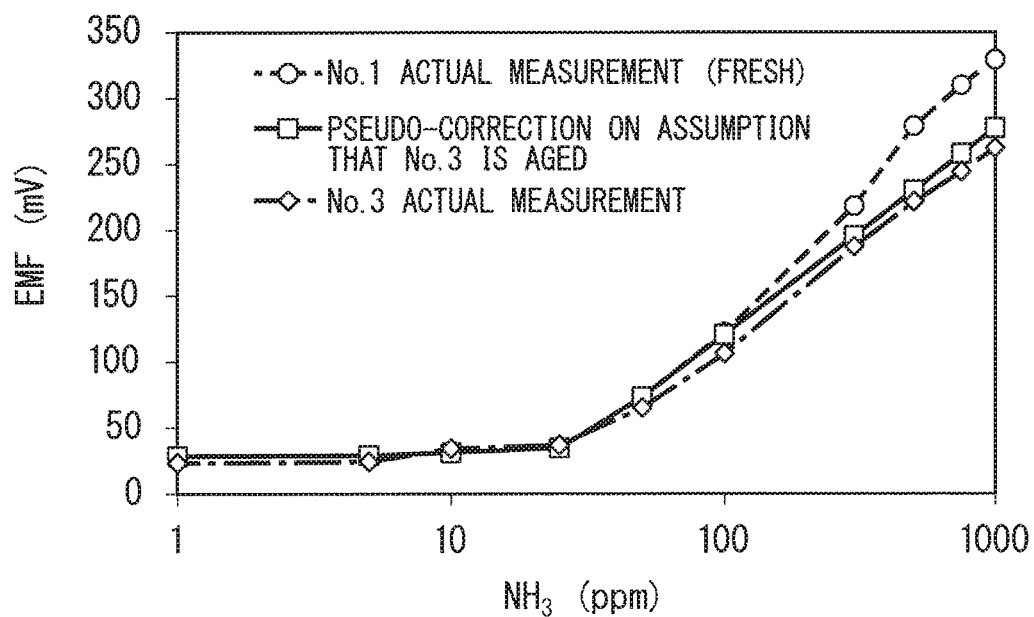
FIG. 10B shows a result of calibration of an ammonia sensor No. 3.

When FIGS. 13A, 13B, 14A, and 14B are respectively compared with FIGS. 10A, 10B, 11A, and 11B, it is confirmed that, as for the sensor No. 2, there is little difference between the result obtained in the present example shown in FIG. 13A and the result obtained in Example 1 shown in FIG. 10A, but, as for the remaining three sensors, the sensor output characteristics obtained in the present example more suitably match the sensor output characteristics of the sensors obtained by actual measurement.

The results indicate that limitation of the oxygen concentration of the exhaust gas is effective in performing the calibration based on the equation (4).

While the invention has been shown and described in detail, the foregoing description is in all aspects illustrative and not restrictive. It is therefore understood that numerous modifications and variations can be devised without departing from the scope of the invention.

What is claimed is:

1. An ammonia sensor calibration method of calibrating output characteristics of an ammonia sensor for an ammonia gas, said ammonia sensor being located downstream from a selective catalytic reduction denitration apparatus (SCR) on an exhaust path of a diesel engine and being connected to a controller having a storage, a relationship between a logarithmic value of a concentration of a predetermined gas component in an exhaust gas exhausted from said diesel engine and a sensor output value from said ammonia sensor when said predetermined gas component is detected being defined as sensor output characteristics for said predetermined gas component, the ammonia sensor calibration method comprising the steps of:

(a) specifying in advance, by the controller, a first value ($\Delta^{t1}_{HC}$) of a first slope in a linear area of said sensor output characteristics for a mixed atmosphere of carbon monoxide and total hydrocarbons and a second value ($\Delta^{t1}_{NH}$) of a second slope in said linear area of said sensor output characteristics for an ammonia gas at a time when an arbitrary time t1 has elapsed since a start of use of said diesel engine and storing the specified first value ($\Delta^{t1}_{HC}$) of the first slope and the specified second value ($\Delta^{t1}_{NH}$) of the second slope in the storage of the controller; and (b) performing calibration of said ammonia sensor when a time t2 has elapsed since said start of use of said diesel engine, said time t2 being greater than said time t1, wherein said step (b) includes:

(b-1) performing detection by said ammonia sensor to generate the sensor output value;

(b-2) specifying, by the controller, a third value ($\Delta^{t2}_{HC}$) of a third slope in said linear area of said sensor output characteristics for said mixed atmosphere;

(b-3) calculating, by the controller, a fourth value ($\Delta^{t2}_{NH}$) from an equation $\Delta^{t2}_{NH} = \Delta^{t2}_{HC}/(\Delta^{t1}_{HC}/\Delta^{t1}_{NH})$; and (b-4) determining, by the controller, the fourth value ($\Delta^{t2}_{NH}$) calculated in said step (b-2) as corresponding to a fourth slope in said linear area of said sensor output characteristics of said ammonia sensor for said ammonia gas.

2. The ammonia sensor calibration method according to claim 1, wherein
said time t1 is 0, and, in said step (a), a fifth value ($\Delta^{f}_{HC}$) and a sixth value ($\Delta^{f}_{NH}$) which are respectively values at a start of use of said ammonia sensor are set as the first value ($\Delta^{t1}_{HC}$) of said first slope and as the second value ($\Delta^{t1}_{NH}$) of the second slope, respectively.

3. The ammonia sensor calibration method according to claim 2, wherein
in said steps (a) and (b-2), a concentration of said mixed atmosphere is specified by detecting said mixed atmosphere using a hydrocarbon gas sensor located along said exhaust path.

4. The ammonia sensor calibration method according to claim 2, wherein
in said steps (a) and (b-2), the first value ($\Delta^{t1}_{HC}$) of the first slope and the third value ($\Delta^{t2}_{HC}$) of the third slope are specified based on a concentration of said mixed atmosphere for calibration formed when fuel is intentionally injected from said diesel engine and said sensor output value from said ammonia sensor at a time when said mixed atmosphere is detected.

5. The ammonia sensor calibration method according to claim 4, wherein
in said steps (a) and (b-2), said concentration of said mixed atmosphere is specified by detecting said mixed atmosphere using a hydrocarbon gas sensor located along said exhaust path.

6. The ammonia sensor calibration method according to claim 4, wherein in said steps (a) and (b-2), the first value ($\Delta^{t1}_{HC}$) of the first slope and the third value ($\Delta^{t2}_{HC}$) of the third slope are specified while maintaining an oxygen concentration of said exhaust gas in a range of 12% to 21% inclusive.

7. The ammonia sensor calibration method according to claim 6, wherein
in said steps (a) and (b-2), said concentration of said mixed atmosphere is specified by detecting said mixed atmosphere using a hydrocarbon gas sensor located along said exhaust path.

8. The ammonia sensor calibration method according to claim 1, wherein
in said steps (a) and (b-2), the first value ($\Delta^{t1}_{HC}$) of the first slope and the third value ($\Delta^{t2}_{HC}$) of the third slope are specified based on a concentration of said mixed atmosphere for calibration formed when fuel is intentionally injected from said diesel engine and said sensor output value from said ammonia sensor at a time when said mixed atmosphere is detected.

9. The ammonia sensor calibration method according to claim 8, wherein
in said steps (a) and (b-2), said concentration of said mixed atmosphere is specified by detecting said mixed atmosphere using a hydrocarbon gas sensor located along said exhaust path.

10. The ammonia sensor calibration method according to claim 8, wherein
in said steps (a) and (b-2), the first value ($\Delta^{t1}_{HC}$) of the first slope and the third value ($\Delta^{t2}_{HC}$) of the third slope are specified while maintaining an oxygen concentration of said exhaust gas in a range of 12% to 21% inclusive.

11. The ammonia sensor calibration method according to claim 10, wherein
in said steps (a) and (b-2), said concentration of said mixed atmosphere is specified by detecting said mixed atmosphere using a hydrocarbon gas sensor located along said exhaust path.

12. The ammonia sensor calibration method according to claim 1, wherein
in said steps (a) and (b-2), a concentration of said mixed atmosphere is specified by detecting said mixed atmosphere using a hydrocarbon gas sensor located along said exhaust path.

13. The ammonia sensor calibration method according to claim 1, wherein
after the step (b), the controller controls an amount of reductant supplied to the SCR.

14. The ammonia sensor calibration method according to claim 13, wherein the reductant is urea.

15. The ammonia sensor calibration method according to claim 1, wherein
during the step (b), the controller suspends a supply of reductant to the SCR.

16. The ammonia sensor calibration method according to claim 15, wherein the reductant is urea.

17. The ammonia sensor calibration method according to claim 15, wherein
after the step (b), the controller resumes the supply of reductant to the SCR.

18. The ammonia sensor calibration method according to claim 17, wherein the reductant is urea.

* * * * *